United States Patent
Baleux et al.

(10) Patent No.: US 9,078,928 B2
(45) Date of Patent: Jul. 14, 2015

(54) CONJUGATED MOLECULES COMPRISING A PEPTIDE DERIVED FROM THE CD4 RECEPTOR COUPLED TO A POLYANIONIC POLYPEPTIDE FOR THE TREATMENT OF AIDS

(75) Inventors: Françoise Baleux, Paris (FR); Hugues Lortat-Jacob, Montbonnot (FR); David Bonnaffe, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 14/005,688

(22) PCT Filed: Mar. 16, 2012

(86) PCT No.: PCT/EP2012/054674
§ 371 (c)(1),
(2), (4) Date: Dec. 13, 2013

(87) PCT Pub. No.: WO2012/126833
PCT Pub. Date: Sep. 27, 2012

(65) Prior Publication Data
US 2014/0107043 A1    Apr. 17, 2014

Related U.S. Application Data

(60) Provisional application No. 61/590,992, filed on Jan. 26, 2012.

(30) Foreign Application Priority Data

Mar. 18, 2011 (EP) .................................... 11305309

(51) Int. Cl.
| | | |
|---|---|---|
| A61K 47/48 | (2006.01) | |
| A61K 38/19 | (2006.01) | |
| A61K 38/16 | (2006.01) | |
| C07K 17/02 | (2006.01) | |
| A61K 38/17 | (2006.01) | |
| C07K 14/73 | (2006.01) | |
| C07K 14/74 | (2006.01) | |

(52) U.S. Cl.
CPC ........... *A61K 47/48276* (2013.01); *A61K 38/16* (2013.01); *A61K 38/177* (2013.01); *A61K 38/195* (2013.01); *A61K 47/48* (2013.01); *A61K 47/48007* (2013.01); *A61K 47/48169* (2013.01); *A61K 47/48238* (2013.01); *C07K 14/70514* (2013.01); *C07K 14/70539* (2013.01); *C07K 17/02* (2013.01); *C07K 2319/00* (2013.01)

(58) Field of Classification Search
None
See application file for complete search history.

(56) References Cited

FOREIGN PATENT DOCUMENTS

| | | | |
|---|---|---|---|
| EP | 2 087 911 | 8/2009 | |
| EP | 2087911 A1 * | 8/2009 | ............ A61K 47/48 |
| WO | WO 2008/015273 | 2/2008 | |
| WO | WO 2009/098147 | 8/2009 | |

OTHER PUBLICATIONS

Betts et al., "Chap. 14: Amino Acid Properties and Consequences of Substitutions," Bioinformatics for Geneticists, Barnes et al., eds., John Wiley & Sons, pp. 289-316 (2003).*
Cormier et al., "Specific interaction of CCR5 amino-terminal domain peptides containing sulfotyrosines with HIV-1 envelope glycoprotein gp120," Proc. Natl. Acad. Sci. USA 97:5762-5767 (2000).*
Downs et al., "Chlorine, Bromine, Iodine, and Astatine," Comprehensive Inorganic Chemistry, Bailar et al., eds., vol. 2, Pergamon Press, Ltd., pp. 1107-1116 (1973).*
Heslop et al., "The Halogens," Inorganic Chemistry, 3rd Ed., Elsevier Publishing Co., pp. 515-520 (1967).*
Politzer et al., "An overview of halogen binding," J. Mol. Model. 13:305-311 (2007).*
Baleux et al., "A synthetic CD4-heparan sulfate glycoconjugate inhibits CCR5 and CXCR4 HIV-1 attachment and entry", *Nature Chemical Biology*, 5(10), pp. 743-748 (2009).
Leydet et al., "Polyanion Inhibitors of Human Immunodeficiency Virus and Other Viruses. Part 2. Polymerized Anionic Surfactants Derived from Amino Acids and Dipeptides", *J. Med. Chem.*, 39(8), pp. 1626-1634 (1996).
Tamalet et al., "Resistance of HIV-1 to multiple antiretroviral drugs in France: a 6-year survey (1997-2002) based on an analysis of over 7000 genotypes", *AIDS*, 17, pp. 2383-2388 (2003).
Huang et al.. "Scorpion-Toxin Mimics of CD4 in Complex with Human Immunodeficiency Virus gp120 Crystal Structures, Molecular Mimicry, and Neutralization Breadth", *Structure*, 13(5), pp. 755-768 (2005).
Chan et al., "Fmoc Solid Phase Peptide Synthesis", *Oxford University Press*, (relevant parts only)(2000).
Vivès et al., "A Novel Strategy for Defining Critical Amino Acid Residues Involved in Protein/Glycosaminoglycan Interactions", *The Journal of Biological Chemistry*, vol. 279, No. 52, pp. 54327-54333 (2004).
Barrè-Sinoussi F. et al., "Isolation of a T-Lymphotropic From a Patient at Risk for Acquired Immune Deficiency Syndrome (AIDS)", *Science*, vol. 220, pp. 868-871 (1983).

(Continued)

*Primary Examiner* — James H Alstrum Acevedo
*Assistant Examiner* — Thea D' Ambrosio
(74) *Attorney, Agent, or Firm* — Finnegan, Henderson, Farabow, Garrett & Dunner, L.L.P.

(57) ABSTRACT

This invention relates to a conjugated molecule comprising a peptide derived from the CD4 receptor coupled to an organic molecule by means of a linker as well as a process for its preparation. Said organic molecule comprises a 5 to 21 amino acid anionic polypeptide. Such a conjugated molecule can be used in antiviral treatment, namely in the treatment of AIDS.

14 Claims, 7 Drawing Sheets

(56) References Cited

OTHER PUBLICATIONS

Gartner S. et al., "The Role of Mononuclear Phagocytes in HTLV-III/LAV Infection", *Science*, vol. 233, pp. 215-219 (1986).

Kärber G., "Contribution to the collective treatment of pharmacological serial tests", *Arch. Exp. Path. Pharmak.*, vol. 162, pp. 480-483 (1931).

* cited by examiner

A

B

C

D

E

F

G

H

CONJUGATED MOLECULES COMPRISING A PEPTIDE DERIVED FROM THE CD4 RECEPTOR COUPLED TO A POLYANIONIC POLYPEPTIDE FOR THE TREATMENT OF AIDS

CROSS REFERENCE TO RELATED APPLICATIONS

This application is a national phase application based on PCT/EP2012/054674, filed Mar. 16, 2012, which claims priority to EP 11305309.4 filed Mar. 18, 2011 and the benefit of U.S. Provisional Application No. 61/590,992, filed Jan. 26, 2012; the content of all of which is incorporated herein by reference.

This invention relates to a conjugated molecule comprising a peptide derived from the CD4 receptor and an organic molecule, such as a polyanionic polypeptide. Such a conjugated molecule can be used in antiviral treatment, namely in the treatment of AIDS. This invention further relates to processes for the preparation of the conjugated molecule.

Triple therapies combining nucleoside (NRTI), non-nucleoside (NNRTI) and/or protease inhibitors (PI) result in a reduction in viral charge beneath levels of detection in a large number of seropositive HIV patients. These therapies target reverse transcription and proteolysis at the same time. Their efficacy has led to a substantial decrease in the number of deaths resulting from HIV infection. Unfortunately, about 80% of the patients show genotypes with antiviral resistance and, more worryingly, 45.5% of viral populations are resistant to NRTI/PI combinations while 26% are resistant to a combination of three anti-HIV classes (Tamalet et al., AIDS. 2003 Nov. 7; 17(16):2383-8). This observation is particularly disturbing since the adverse effects of long-term triple therapy treatment (lipoatrophy, lipodystrophy, hypertriglyceridaemia, hypercholesterolaemia, neuropathy, etc.) found in 70% of patients receiving the treatment result in poor compliance and "sudden" discontinuation of treatment which often leads to resistance. The development of less severe forms of treatment with fewer adverse effects and without cross-resistance is therefore a priority despite the large number of currently available medications on the market. With this in mind, it is essential to target HIV replication steps other than reverse transcription and proteolysis.

Entry of a virus into a cell is a crucial step in the viral infection cycle. This process is divided into two phases: first, the virus interacts with specific host receptors at the cell surface, followed by penetration of the viral genetic material into the target cell. With HIV, the molecular partners involved in the mechanisms of adhesion and entry are well established. The gp120 viral envelope glycoprotein essentially determines the virus/cell interaction complex, by binding to a transmembrane glycoprotein of the host cell, CD4.

This interaction leads to a conformational change in gp120 which exposes a particular epitope, called CD4-induced (CD4i), thus creating a binding site for chemokine receptors (essentially CCR5 and CXCR4). CCR5 and CXCR4 therefore act as gp120 co-receptors at the cell surface. This second interaction leads to re-organization of the gp120/gp41 protein complex and initiation of cell/virus membrane fusion.

The cellular tropism of the HIV virus is defined by the type of co-receptor used. So-called X4 or <<T-tropic>> viruses tend to infect more specifically cell lines expressing CXCR4 at their surface, such as the T lymphocytes. So-called R5 or <<M-tropic>> viruses use co-receptor CCR5 and mainly infect macrophages and monocytes. The presence of R5 or X4 viruses is generally associated with quite distinct stages of AIDS development (asymptomatic phase for R5, appearance of X4 virus often linked to unfavourable evolution outcome of the disease, suggesting that use of co-receptor CXCR4 is an important factor in the pathogenesis of AIDS). As the structural determinants for recognition of CCR5 and CXCR4 are carried by gp120, the R5 and X4 viruses represent two separate targets.

It was shown in international patent application WO 2008/015273 that particular activated peptides derived from the CD4 receptor can react selectively with organic molecules affording chemically defined covalent conjugates. This activation requires the insertion of one and only one residue of the amino acid lysine in a defined position in the sequence of the peptide derived from the CD4 receptor. This insertion allows the coupling of organic compounds through linkers and chemistries after the miniCD4 synthesis and purification.

Numerous potential antiviral derivatives, consisting of conjugated molecules comprising a CD4 peptide specifically coupled to polyanionic heparan sulphate (HS) by means of a linker were disclosed in WO 2009/098147. These conjugates show potent antiviral activity. The use of HS was motivated by the presence of at least two different HS recognition sites in gp120, namely the V3 variable loop and the site induced by CD4 (CD4i): the CD4 moiety of the mCD4-HS is thought to trigger conformational changes in gp120 by direct interaction, thus resulting in exposure of the CD4i epitope, with which the covalently bound HS can then interact, thereby impairing HIV virus infection of X4 and R5 cell lines.

This approach consisting in inhibiting viral attachment to cells is therapeutically advantageous, since it directly targets the virus and not the cells themselves. It is therefore devoid of the cellular effects observed with medication which binds to co-receptors. In addition, in view of the preservation of the sites involved as a function of various viral tropisms, the compounds according to the invention should interact with the gp120 of different viral isolates. While it might be misleading to think that resistance will never arise, it can nevertheless be expected that it should occur at a much lower rate than with other treatments. Indeed, the CD4 site of gp120 has to remain intact in order to continue to bind to CD4, like the basic residues involved in binding to the polyanionic polysaccharide for interaction with the co-receptors. Mutation in any of these two sites should indeed result in a virus with reduced infectivity.

The present Inventors have now identified a new conjugated molecule capable of blocking the entry of the HIV virus into the cells. They show that the presence of heparan sulphate oligosaccharides in the mCD4 conjugated molecule is not absolutely required for inhibiting the virus entry into X4 or R5 cell lines and that very effective antiviral activity can also be obtained by replacing the previously used HS molecule by anionic polypeptides consisting of 5 to 21, advantageously 5 to 17, notably 5, 9, 13, 17 or 21, and preferably 13 amino acids. In a preferred embodiment, some amino acids are negatively charged, notably at least 1, advantageously at least 2, and preferably at least 3. In more preferred embodiments, 3, 4, 5, 6, 7, 8, 9, 10, 11, 12 or 13 amino acids are negatively charged (depending on the length of the anionic polypeptide). In the most preferred embodiment 9 amino acids are negatively charged when the anionic polypeptide consists of 13 amino acids. More importantly, they have shown that, surprisingly, these new mCD4 conjugated molecules (comprising the said anionic polypeptides) have a better antiviral activity against both R5 or X4 viruses than the conjugated molecules disclosed in the prior art.

According to a first aspect, the invention covers a conjugated molecule comprising a peptide derived from the CD4 receptor, said peptide being coupled to an organic molecule by means of a linker, wherein:
  the said peptide derived from the CD4 receptor comprises the following general sequence (I):

(I)
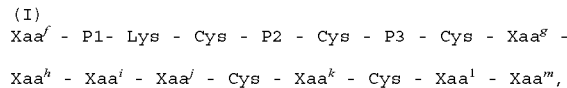

in which:
  P1 represents 3 to 6 amino acid residues,
  P2 represents 2 to 4 amino acid residues,
  P3 represents 6 to 10 amino acid residues,
  $Xaa^f$ represents N-acetylcysteine (Ac-Cys) or thiopropionic acid (TPA),
  $Xaa^g$ represents Ala or Gln,
  $Xaa^h$ represents Gly or (D)Asp or Ser,
  $Xaa^i$ represents Ser or His or Asn,
  $Xaa^j$ represents biphenylalanine (Bip), phenylalanine or [beta]-naphthylalanine,
  $Xaa^k$ represents Thr or Ala,
  $Xaa^l$ represents Gly, Val or Leu, and
  $Xaa^m$ represents —$NH_2$ or —OH,
  the amino acid residues in P1, P2 and P3 being natural or non-natural, identical or different, said residues of P1, P2 and P3 being all different from the Lys residue and P1, P2 and P3 having a sequence in common or not, and
  the said organic molecule comprises
    an anionic polypeptide consisting of 5 to 21, advantageously 5 to 17, and preferably 13 amino acid residues being natural or non-natural, identical or different, wherein at least 3, and notably 3 to 15, such as 3 to 13 amino acids are negatively charged,
    a molecular group A-Z, wherein:
      A comprises a group chosen between the groups of formula —$CO(CH_2)_3NH$—$CO(CH_2)_2$—, —$CO(CH_2)_p$—NH—CO—$(CH_2)_q$—, —$CO(CH_2$—$CH_2)$—(O—$CH_2$—$CH_2)_p$—NH—CO—$(CH_2)_q$—, —$CO(CH_2)_p$—NH—CO—$(CH_2$—$CH_2$—O$)_q$—$(CH_2$—$CH_2)$— and —$CO(CH_2$—$CH_2)$—(O—$CH_2$—$CH_2)$—NH—CO—$(CH_2$—$CH_2$—O$)_q$—$(CH_2$—$CH_2)$—, wherein p represents an integer comprised between 1 and 10 and q represents an integer comprised between 1 and 10, and wherein the first carbonyl group is coupled to the alpha $NH_2$ of N-terminal Serine, and advantageously A represents a group of formula —$CO(CH_2)_3NH$—$CO(CH_2)_2$— and
      Z represents an halogen atom, a thiol or a maleimide group,
the said anionic polypeptide being linked to the linker by the said molecular group of formula A-Z, and the said linker being covalently bound at one of its extremity to the free amino group (—$NH_2$) of the amino acid residue Lys present in general sequence (I) of the said peptide derived from the CD4 receptor, and being covalently bound at its other extremity to the Z group of the said organic molecule.

Preferably, P3 comprises at least one basic amino acid, said basic amino acid being even more preferably arginine. The presence of basic residues in this portion of the CD4 receptor fragment contributes to its binding to the gp120 protein. The inventors therefore prefer to introduce at least one basic amino acid into P3, preferably arginine. This maintains thus a basic moiety which is not reactive at derivation at pH 7-8 but which has been found to be useful for the binding of miniCD4 peptide to the gp120 protein.

In this application, the terms "miniCD4 peptide", "CD4 peptide" and "miniCD4" are used interchangeably to designate the peptide derived from the CD4 receptor comprising or consisting of general sequence (I) defined above.

As disclosed in WO 2009/098147, it is required that the miniCD4 peptide of the invention contains one and only one lysine (Lys) amino acid residue, and that said lysine is in the position as defined in general sequence (I). The Cys residues in general sequence (I) allow the formation of three disulphide bridges needed for folding back of miniCD4. Thiopropionic acid (TPA), when it is in the N-terminus position of the peptide of general sequence (I), makes it possible to reduce hindrance in N-ter and overcome the presence of an amine group. Thus, according to a preferred embodiment, $Xaa^f$ represents TPA in general sequence (I).

Bip increases contact with glycoprotein gp120 in the cavity where the Phe 43 of CD4 receptor is lodged. Thus, in a preferred embodiment, $Xaa^j$ represents Bip. Nevertheless, it may be advantageous to have Phe as $Xaa^j$ in general sequence (I), since a structural analysis suggests that such a miniCD4 may mimic CD4 efficiently (Huang C C et al., Structure. 2005 May; 13(5):755-68). Thus according to another preferred embodiment, $Xaa^j$ represents Phe.

The peptide of general sequence (I) derived from the CD4 receptor forms an alpha helix structure followed by a beta sheet. The amino acids $Xaa^g$-$Xaa^h$-$Xaa^i$-$Xaa^j$-Cys-$Xaa^k$-Cys-$Xaa^l$ participate in a major way to the binding to gp120. These peptides display an $IC_{50}$ (affinity for gp120) similar to those of sCD4 (soluble CD4).

The CD4 peptide of the invention can be prepared by conventional solid phase chemical synthesis techniques, for example according to the Fmoc solid phase peptide synthesis method ("Fmoc solid phase peptide synthesis, a practical approach", edited by W. C. Chan and P. D. White, Oxford University Press, 2000) and/or by genetic recombination.

Preferably, the said CD4 peptide is chosen from the group consisting of sequences SEQ ID No. 1 and SEQ ID No. 2. More preferably, the CD4 peptide of the invention has the sequence represented by SEQ ID No. 1.

The term "linker" refers in the present invention to a linker obtained by the coupling of a bifunctional compound, as defined below, with a peptide derived from the CD4 receptor and the organic molecule. Thus, the length of the linker varies as a function of the bifunctional compounds used.

In particular, the linker will be advantageously chosen among:

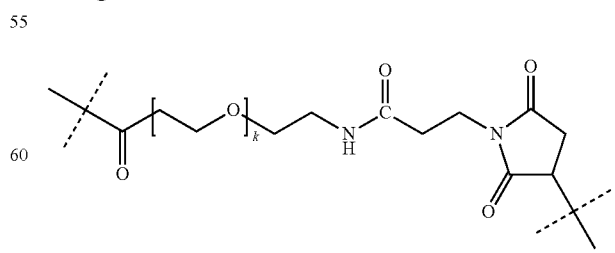

with k representing an integer comprised between 2 and 24, and being advantageously 2, 4, 8 or 12,

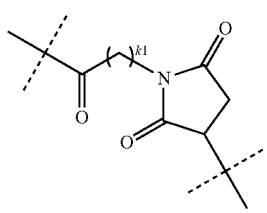

with k1 representing an integer comprised between 1 and 10, thus equal to 1, 2, 3, 4, 5, 6, 7, 8, 9 or 10, and advantageously equal to 1, 2, 3, 5 or 10,

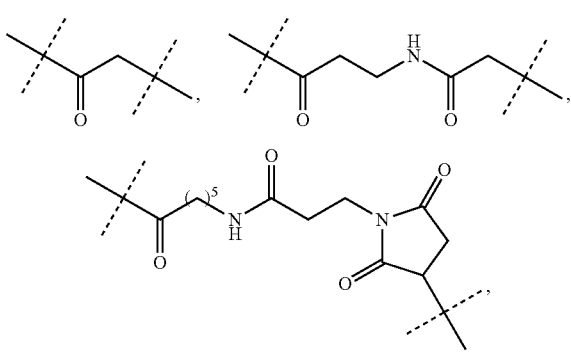

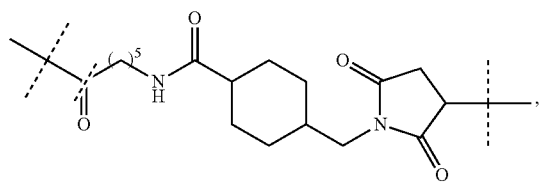

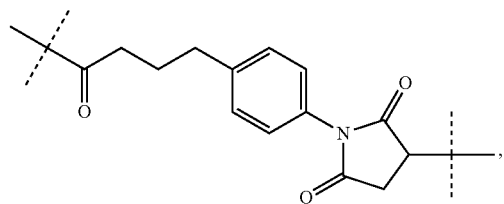

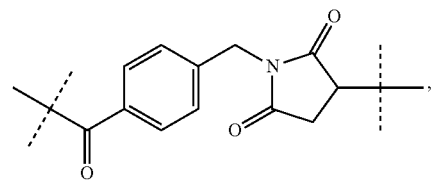

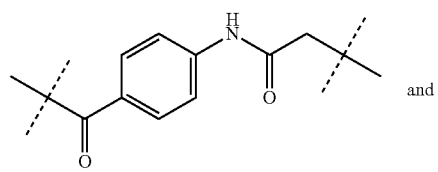

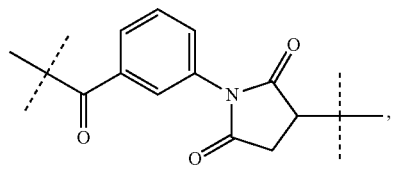

when Z represents a thiol group, and among:

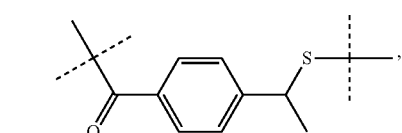

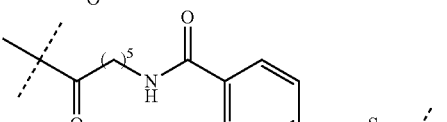

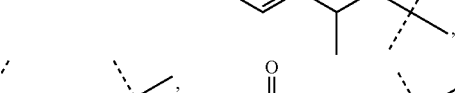

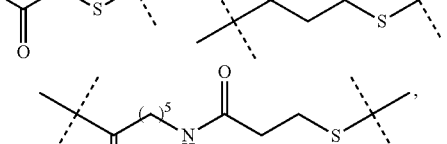

when Z represents a maleimide group or a halogen atom.

In a preferred embodiment, the linker will be chosen among

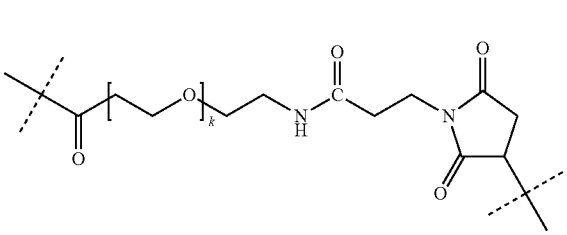

with k representing an integer comprised between 2 and 24, and being advantageously 2, 4, 8 or 12 and

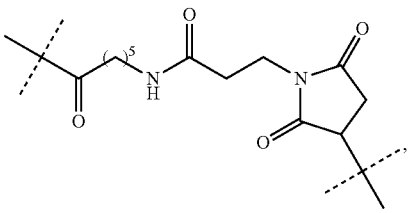

with k1 representing an integer comprised between 1 and 10, thus equal to 1, 2, 3, 4, 5, 6, 7, 8, 9 or 10, and advantageously equal to 1, 2, 3, 5 or 10,
when Z represents a thiol group,
and among:

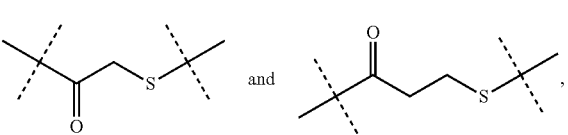

when Z represents a maleimide group or a halogen atom.

Such linkers correspond thus to the use of succinimidyl-6-[beta-maleimidopropionamido]hexanoate (SMPH), NHS-PEO$_n$-maleimide, with n representing an integer comprised between 2 and 24, and being advantageously 2, 4, 8 or 12, SATA (N-succinimidyl-S-acetylthioacetate) and SATP (N-succinimidyl-S-acetylthiopropionate), as bifunctional compound.

In another preferred embodiment, the linker is

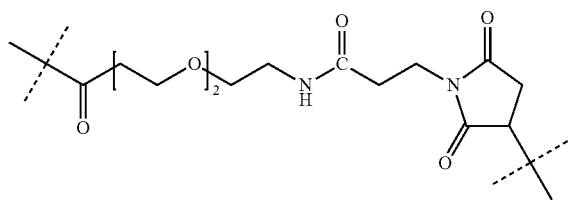

The conjugated molecule of the invention comprises an anionic polypeptide, said anionic peptide consisting of 13 amino acids, wherein 3, 4, 5, 6, 7, 8, 9, 10, 11, 12 or 13 amino acid residues are negatively charged. In a preferred embodiment, the anionic polypeptide consists of 13 amino acids, wherein 9 amino acid residues are negatively charged.

Advantageously, the anionic peptide of the invention is linked to the A group of the compound of formula I by the N-terminal end. Advantageously, the bond formed between the said anionic peptide and the A group is a peptidic bond, and thus involves both the amino (NH$_2$) of the said peptide and the carboxylic group (COOH) on the A group.

Without being bound by theory, it is thought that the said 13 amino acid-long anionic polypeptides impair the interaction between the CD4i exposed site and CXCR4 (or CCR5) chemokine receptors, thereby impairing the initiation of the cell/virus membrane fusion.

In the sense of the present invention, "amino acids" means all natural α-amino acid residues (for example alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophane (Trp), tyrosine (Tyr) and valine (Val)) in D or L form, as well as non-natural amino acids (for example, β-alanine, allylglycine, tert-leucine, norleucine (Nle), 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxylic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxylic acid 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-amino-pyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine, γ-carboxyglutamate, β-cyclohexylalanine, citruline, 2,3-diamino propionic acid, hippuric acid, homocyclohexylalanine, moleucine, homophenylalanine, 4-hydroxyproline, indoline-2-carboxylic acid, isonipecotic acid, sulfotyrosine, aminosuberic acid, p-carboxymethyl phenylalanine, α-methyl-alanine, nicopetic acid, norvaline, octahydroindole-2-carboxylic acid, ornithine, penicillamine, phenylglycine (Phg), 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, the statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4,4',4',4'-hexafluorovaline, pentafluorophenylalanine, 2,3-difluorophenylalanine, 2,4-difluorophenylalanine, 2,5-difluorophenylalanine, 2,6-difluorophenylalanine, 3,4-difluoropheny 1 alanine, 3,5-difluorophenylalanine, 3,3-difluoro-3-(4-fluorophenyl) alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine and hexafluoronorleucine). The term also includes natural and non-natural amino acids carrying a conventional amino protecting group (for example, an acetyl group, tert-butyloxycarbonyl, benzyloxycarbonyl or 9-fluorenylmethylcarbonyl), as well as natural and non-natural amino acids protected at the carboxylic end (advantageously by a $C_1$-$C_{18}$ alkyl group, an ester, a phenyl amide or benzyl amide or an amide, which, respectively, give a carboxylic end of the following formula: —CO($C_1$-$C_{18}$ alkyl), —COO($C_1$-$C_{18}$ alkyl), —CONHphenyl, CONHbenzyl, or $CONH_2$).

As used herein, the term "anionic" designates a negatively charged molecule, which for example migrates to an anode in electrolysis. Also, a "negatively charged" amino acid designates an amino acid which carries a side-chain charge which is negative at a pH of 7.4. Negatively charged amino acid residues according to the invention thus include, for example, aspartic acid, tyrosine, sulfotyrosine, tyrosine sulfonate, aminosuberic acid, p-carboxymethyl phenylalanine, and glutamic acid residues.

As used herein, sulfotyrosine (or 2-amino-3-(4-(sulfooxy) phenyl)propanoic acid) is a non-natural amino acid having the following formula:

[Structure: tyrosine with O-SO₃H substituent]

As used herein, the term "tyrosine sulfonate" (or "2-amino-3-(4-(sulfomethyl)phenyl) propanoic acid") refers to a non natural amino acid having the following formula:

[Structure: phenylalanine derivative with CH₂-SO₂-O⁻ on para position]

According to the present invention, aminosuberic acid is a non-natural amino acid having the following formula:

[Structure: H₂N-CHC(=O)-OH with (CH₂)₅-COOH side chain]

As used herein, p-carboxymethyl phenylalanine refers to a non-natural amino acid having the following formula:

[Structure: phenylalanine with CH₂-COOH on para position]

In one embodiment of the invention, the said anionic polypeptide consists of 13 identical negatively charged amino acids. It can be, for example, the polypeptide consisting of 13 aspartic acid residues (SEQ ID NO: 9), 13 sulfotyrosine residues (SEQ ID NO: 10), 13 tyrosine sulfonate residues (SEQ ID NO: 11), 13 aminosuberic acid residues (SEQ ID NO: 12), 13 p-carboxymethyl phenylalanine residues (SEQ ID NO: 13), and 13 glutamic acid residues (SEQ ID NO: 3). In a preferred embodiment, said identical amino acid is glutamic acid E and the anionic polypeptide of the conjugated molecule of the invention is SEQ ID NO: 3.

In another embodiment of the invention, the anionic peptide of the invention comprises negatively charged and uncharged amino acids. Preferably, the said anionic peptide comprises at least one negatively charged amino acid and at least another amino acid. Preferably, the said other amino acid is an amino acid carrying a polar uncharged side chain. Such amino acids include e.g. serine, threonine, asparagine, and glutamine. In a further preferred embodiment, the said other amino acid is serine or threonine. In a still further preferred embodiment, the said other amino acid is serine. In another preferred embodiment, the negatively charged amino acid is aspartic acid.

In another further preferred embodiment, the said anionic polypeptide of the invention comprises at least two different negatively charged amino acids, in addition to the at least one other amino acid. In this case, said anionic polypeptide has for example the sequence S-(X-D-X-S)$_n$, such as S-X-D-X-S-X-D-X-S-X-D-X-S, where n is an integer comprised between 1 and 5, and preferably is 3, S represents serine, D represents aspartic acid, and X is selected from the group consisting of: tyrosine, sulfotyrosine, tyrosine sulfonate, aminosuberic acid, and p-carboxymethyl phenylalanine (SEQ ID NO: 19) and where the various X groups can be identical or different, preferably identical.

In this embodiment, said anionic polypeptide can have in particular any of the following sequences:

S-(Y$_{SO3}$-D-Y$_{SO3}$-S)$_n$, such as S-Y$_{SO3}$-D-Y$_{SO3}$-S-Y$_{SO3}$-D-Y$_{SO3}$-S-Y$_{SO3}$-D-Y$_{SO3}$-S (SEQ ID NO: 4), where Y$_{SO3}$ is sulfotyrosine;

S-(Y$_{SN}$-D-Y$_{SN}$-S)$_n$, such as S-Y$_{SN}$-D-Y$_{SN}$-S-Y$_{SN}$-D-Y$_{SN}$-S-Y$_{SN}$-D-Y$_{SN}$-S (SEQ ID NO: 5), where Y$_{SO3}$ is tyrosine sulfonate;

S-(pF-D-pF-S)$_n$, such as S-pF-D-pF-S-pF-D-pF-S-pF-D-pF-S (SEQ ID NO: 6), where pF is p-carboxymethyl phenylalanine;

S-(Asu-D-Asu-S)$_n$, such as S-Asu-D-Asu-S-Asu-D-Asu-F-Asu-F-D-Asu-S (SEQ ID NO: 7), where Asu is aminosuberic acid; and S-(Y-D-Y-S)$_n$, such as S-Y-D-Y-S-Y-D-Y-S-Y-D-Y-S (SEQ ID NO: 8), where Y is tyrosine.

The anionic polypeptide can have also the following sequences:

S-Y$_{SO3}$-D-Y$_{SO3}$-S-Y$_{SO3}$-D-Y-S-Y-D-Y-S (SEQ ID NO: 20), or

S-Y-D-Y-S-Y-D-Y$_{SO3}$-S-Y$_{SO3}$-D-Y$_{SO3}$-S (SEQ ID NO: 21).

Most preferably according to the invention, X represents sulfotyrosine. Therefore, in the most preferred embodiment, the anionic polypeptide of the invention has the sequence: S—(Y$_{SO3}$-D-Y$_{SO3}$-S)$_n$, and in particular S—Y$_{SO3}$-D-Y$_{SO3}$-S—Y$_{SO3}$-D-Y$_{SO3}$-S-Y$_{SO3}$-D-Y$_{SO3}$-S (SEQ ID NO: 4).

In a particular embodiment, the conjugated molecule of the invention comprises a peptide derived from the CD4 receptor, said peptide being coupled to an organic molecule by means of a linker, wherein:

the peptide derived from the CD4 receptor is chosen from the group consisting of sequences SEQ ID NO: 1 and SEQ ID NO: 2, the linker is CO—(CH$_2$O)$_2$CH$_2$NHCO(CH$_2$)$_2$-pyrrolidinyl-2,5-dione, the organic molecule comprises an anionic polypeptide having a sequence selected from the group consisting of: S-(Y$_{SO3}$-D-Y$_{SO3}$-S)$_n$, S-(Y$_{SN}$-D-Y$_{SN}$-S)-S-(pF-D-pF-S)-S-(Asu-D-Asu-S)$_n$, and S-(Y-D-Y-S)$_n$; and in particular selected from the group consisting of: S-Y$_{SO3}$-D-Y$_{SO3}$-S-Y$_{SO3}$-D-Y$_{SO3}$-S-Y$_{SO3}$-D-Y$_{SO3}$-S (SEQ ID NO 4), S-Y$_{SN}$-D-Y$_{SN}$-S-Y$_{SN}$-D-Y$_{SN}$-S-Y$_{SN}$-D-Y$_{SN}$-S (SEQ ID NO: 5), S-pF-D-pF-S-pF-D-pF-S-pF-D-pF-S (SEQ ID NO: 6), S-Asu-D-Asu-S-Asu-D-Asu-F-Asu-F-D-Asu-S (SEQ ID NO: 7), S-Y-D-Y-S-Y-D-Y-S-Y-D-Y-S (SEQ ID NO: 8), said sequence being linked to the linker by a molecular group of formula A-Z, wherein A is —NHCO(CH$_2$)$_3$NH—CO(CH$_2$)$_2$— and Z is a thiol group.

In a preferred embodiment, the conjugated molecule of the invention comprises the peptide derived from the CD4 receptor chosen from the group consisting of sequences SEQ ID No. 1 and SEQ ID No. 2, said peptide being coupled to an organic molecule by means of the linker CO—(CH$_2$O)$_2$CH$_2$NHCO(CH$_2$)$_2$pyrrolidinyl-2,5-dione, and an anionic polypeptide having the sequence S—(Y$_{SO3}$-D-Y$_{SO3}$-S)$_n$, and in particular S—Y$_{SO3}$-D-Y$_{SO3}$-S-Y$_{SO3}$-D-Y$_{SO3}$-S-Y$_{SO3}$-D-Y$_{SO3}$-S (SEQ ID NO 4), said sequence being linked to the linker by a molecular group of formula A-Z, wherein A is —NHCO(CH$_2$)$_3$NH—CO(CH$_2$)$_2$— and Z is a thiol group.

The conjugates of the invention are capable of inhibiting HIV entry into the cell, by blocking the attachment of the virus on the cell membrane and thereby the virus entry. The conjugates of the invention can therefore be used in therapy. More preferably, the conjugates of the invention can be used for treating viral infections. Even more preferably, the said conjugates can be used for treating AIDS. Therefore, according to a second aspect, the invention covers a conjugated molecule as defined above for its use as medicament. The invention also relates to the conjugates as defined above for treating viral infections, and, in particular, for the treatment of AIDS. The use of a conjugated molecule as defined above for the manufacture of a medicament for an antiviral treatment, and in particular for the treatment of AIDS, is also an object of the present invention.

According to a third aspect, the invention covers a pharmaceutical composition comprising a conjugated molecule as defined above and a pharmaceutically acceptable vehicle. This composition can be used as a medicament, preferably for the treatment of viral infections, and, more preferably, for the treatment of AIDS.

In the pharmaceutical compositions of the present invention for oral, intranasal, sublingual, subcutaneous, intramuscular, intravenous, transdermal, local or rectal administration, the active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

The pharmaceutical composition of the invention may contain, in addition to the carrier and conjugate of the invention, various diluents, fillers, salts, buffers, stabilizers, solubilizers, and other materials well known in the art.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18$^{th}$ and 19$^{th}$ editions thereof, which are incorporated herein by reference.

The conjugated molecule in the composition preferably is formulated in an effective amount. An "effective amount" refers to an amount effective, at dosages and for periods of time necessary, to achieve the desired result, such as induction of apoptosis in tumor cells. A "therapeutically effective amount" means an amount sufficient to influence the therapeutic course of a particular disease state. A therapeutically effective amount is also one in which any toxic or detrimental effects of the agent are outweighed by the therapeutically beneficial effects.

Dosage regimens may be adjusted to provide the optimum response. For example, a single bolus may be administered, several divided doses may be administered over time, or the dose may be proportionally reduced or increased. The compositions of the invention can be administered to a subject to affect viral infection in a subject. As used herein, the term "subject" is intended to include living organisms which is susceptible to viral infection, and specifically includes mammals, such as rabbits, dogs, cats, mice, rats, monkey transgenic species thereof, and preferably humans.

For therapeutic applications, the conjugated molecule of the invention is administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerebrospinal, subcutaneous, intraarticular, intrasynovial, intrathecal, oral, topical, or inhalation routes.

The invention also relates to an antiviral treatment method, preferably an anti-AIDS treatment method, comprising the administration to a patient in need thereof of a conjugated molecule according to the invention or the pharmaceutical composition containing it.

In a fourth aspect, the invention provides a process for the preparation of a conjugated molecule as defined above, characterized in that the process comprises the following steps:

a. contacting the miniCD4 peptide of general sequence (I) as defined above with a bifunctional compound carrying two active groups, so that one of the two active groups forms a covalent bond with the free amino group (—NH$_2$) of the residue of the amino acid Lys present in general sequence (I), in order to obtain an activated peptide carrying the second active group of the bifunctional group, and b. contacting the activated peptide obtained at step (a) with an organic molecule carrying a functional group as defined above carrying a thiol group for which the thiol group (SH) has been protected by a protective thiol group, so that the active group of the activated peptide forms a covalent bond with the functional group, protected or not, of the organic molecule, in order to obtain the conjugated molecule.

The compound obtained at step (a) will be called indifferently, in the present application, "activated peptide", "activated miniCD4", "activated CD4 peptide" or "activated miniCD4 peptide".

The functional group according to the invention refers to a halogen atom, a maleimide, a thiol or a protective thiol group.

The term "protective thiol group", as used in the present invention refers to a sulfur atom substituted by a S-protecting group in order to protect a thiol group against undesirable reactions during synthetic procedures. Commonly used S-protecting groups are disclosed in Greene, "Protective Groups In Organic Synthesis" (John Wiley & Sons, New York (1981)). S-protecting groups comprise benzyl ethers, substituted or not, such as p-methoxybenzyl or p-nitrobenzyl, trityl ethers, thioethers, thioacetate or thioacetal. Advantageously, the protected thiol group is a thioacetyl.

When the organic compound carries a protective thiol group, said protective group will be deprotected before or during step (b), in order to recover a free thiol group and to allow the coupling of this thiol with the active group of the activated peptide.

The characteristics of the peptide derived from CD4 receptor are the same as defined above. In particular, P3 comprises preferably at least one basic amino acid, said basic amino acid being even more preferably arginine. According to a preferred embodiment, Xaa$^f$ represents TPA in general sequence (I). According to another preferred embodiment, Xaa$^j$ represents Phe. Preferably, the sequence of the peptide derived from the CD4 receptor of general sequence (I) is chosen from the group consisting of sequences SEQ ID NO: 1 and SEQ ID NO: 2, advantageously SEQ ID NO: 1.

The term "bifunctional compound" in this patent application refers to any compound incorporating two active groups wherein one of the two active groups is capable of forming a covalent bond with the free amino group (—NH$_2$) of the residue of the amino acid Lys present in general sequence (I) and the other active group is capable of forming a covalent bond with the organic molecule.

The person skilled in the art knows well the bifunctional compounds which can be used within the framework of this invention. Namely, the bifunctional compound according to this invention can be chosen from the following non-limiting list: NHS-PEO$_n$-Maleimide where n is comprised between 2 and 24, advantageously n=2, 4, 8 or 12, Sulfo-KMUS (N-[k-maleimidoundecanoyloxy]sulfosuccinimide ester), LC-SMCC (succinimidyl-4-[N-maleimidomethyl]cyclohexane-1-carboxy-[6-amidocaproate]), KMUA (N-k-maleimidoundecanoic acid), SMPB (succinimidyl 4[p-maleimidophenyl]butyrate), Sulfo-SMPB (sulfosuccinimidyl 4[p-maleimidophenyl]butyrate), Sulfo-SIAB (N-sulfosuccinimidyl[4-iodoacetyl]aminobenzoate), SIAB (N-succinimidyl [4-iodoacetyl]aminobenzoate), Sulfo-EMCS ([N-e-maleimidocaproyloxy]sulfosuccinimide ester), EMCA (N-e-maleimidocaproic acid), EMCS ([N-e-maleimidocaproyloxy]succinimide ester), SMCC (succinimidyl 4-[N-maleimidomethyl]cyclohexane-1-carboxylate), Sulfo-SMCC (sulfosuccinimidyl[4N-maleimidomethyl]cyclohexane-1-carboxylate), MBS (m-maleimidobenzoyl-N-hydroxy succinimide ester), Sulfo-MBS (m-maleimidobenzoyl-N-hydroxysulfosuccinimide ester), GMBS (N-[g-maleimidobutyryloxy]succinimide ester), Sulfo-GMBS (N-[g-maleimidobutyryloxy]sulfosuccinimide ester), SPDP (N-succinimidyl-3-(2-pyridyldithio)propionate), SBAP (succinimidyl 3-[bromoacetamido]propionate), BMPS (N-[[beta]-maleimidopropyloxy]succinimide ester), BMPA (N-[beta]-maleimidopropionic acid), AMAS N-(a-maleimidoacetoxy)succinimide ester), SIA (N-succinimidyl iodoacetate), SMPH (succinimidyl-6-[beta-maleimido propionamido]hexanoate), SATA (N-succinimidyl-5-acetylthioacetate) and SATP (N-succinimidyl-S-acetylthiopropionate).

According to the invention, NHS-PEO$_n$-Maleimide wherein n=2 is also called succinimidyl-[(N-maleimidoproprionamido)-diethyleneglycol]ester, NHS-PEO$_n$-Maleimide wherein n=4 is also called succinimidyl-[(N-maleimidoproprionamido)-tetraethyleneglycol]ester, NHS-PEO$_n$-Maleimide wherein n=8 is also called succinimidyl-[(N-maleimidoproprionamido)-octaethyleneglycol]ester, NHS-PEO$_n$-Maleimide wherein n=12 is also called succinimidyl-[(N-maleimidoproprionamido)-dodecaethyleneglycol]ester.

The active group capable of forming a covalent bond with the free amine group (—NH$_2$) of the residue of amino acid Lys present in general sequence (I) can be any active ester group.

Preferably, the active group capable of forming a covalent bond with the free amine group (—NH$_2$) of the residue of amino acid Lys present in general sequence (I) is the active group N-hydroxysuccinimide ester (NHS) or N-hydroxy-4-sulfo-succinimide ester, and advantageously is the NHS active group. Even more preferably, the two active groups of the bifunctional compound are different (heterobifunctional group) and one of the two groups is the NHS active group or a N-hydroxy-4-sulfo-succinimide ester, and advantageously is the NHS active group.

Advantageously, the active group of the bifunctional compound, capable of forming a covalent group with the functional group of the organic molecule, is a halogen atom or a maleimide group when the functional group of the organic molecule is a thiol or a protective thiol group and is a thiol or a protective thiol group, as defined above, when the functional group of the organic molecule is a halogen atom or a maleimide group.

According to a preferred embodiment, when the functional group of the organic molecule is a thiol group or a protective thiol group, the bifunctional compound is chosen from the group consisting of succinimidyl-6[beta-maleimidopropionamido]hexanoate (SMPH) and NHS-PEO$_n$-maleimide, n being comprised between 2 and 24, and advantageously is 2, 4, 8 or 12.

According to a particularly preferred embodiment, the bifunctional compound is SMPH.

The molecular structure of SMPH is as follows:

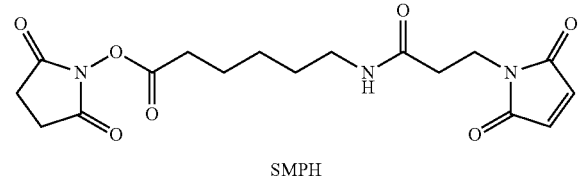 [SMILES: O=C(CCN1C(=O)C=CC1=O)NCCCCCC(=O)ON1C(=O)CCC1=O]

SMPH

According to yet another particularly preferred embodiment, the bifunctional compound is succinimidyl-[(N-maleimidopropionamido)-diethyleneglycol]ester, also called NHS-PEO$_2$-maleimide, succinimidyl-[(N-maleimidopropionamido)-tetraethyleneglycol]ester, also called NHS-PEO$_4$-maleimide, succinimidyl-[(N-maleimidopropionamido)-octaethyleneglycol]ester, also called NHS-PEO$_8$-maleimide, succinimidyl-[(N-maleimidopropionamido)-dodecaethyleneglycol]ester, also called NHS-PEO$_{12}$maleimide, still more preferably the bifunctional compound is NHS-PEO$_2$-maleimide.

The molecular structure of NHS-PEO$_2$-maleimide is as follows:

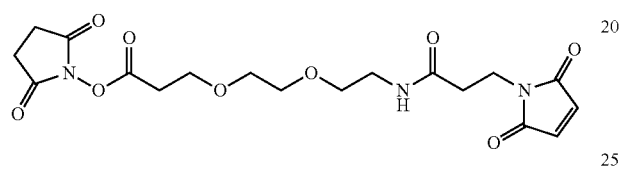

According to another particularly preferred embodiment, when the functional group of the organic molecule is a halogen atom or a maleimide group, the bifunctional compound is chosen from the group consisting of N-succinimidyl-5-acetylthioacetate (SATA) and N-succinimidyl-5-acetylthiopropionate (SATP).

The molecular structure of SATA is as follows:

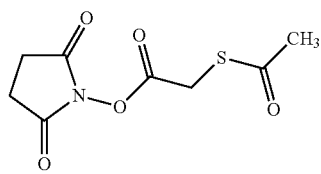

The molecular structure of SATP is as follows:

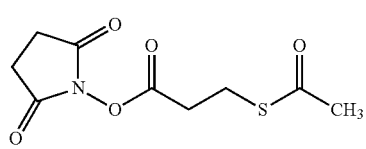 [SMILES: CC(=O)SCCC(=O)ON1C(=O)CCC1=O]

The bifunctional compounds can be obtained from PIERCE (Rockford, Ill.).

Preferably again, the process according to the invention includes a preliminary step for the preparation of the peptide derived from the CD4 receptor of general sequence (I), when Xaa$^f$ represents TPA, said step consisting of contacting the peptide derived from the CD4 receptor of the following general sequence (III):

(III)

P1- Lys - Cys - P2 - Cys - P3 - Cys - Xaa$^g$ - Xaa$^h$ -

Xaa$^i$ - Xaa$^j$ - Cys - Xaa$^k$ - Cys - Xaa$^l$ - Xaa$^m$, where P1 to P3 and Xaa$^g$ to Xaa$^m$ are as defined in general sequence (I), with N-succinimidyl-3-(2-pyridyldithio)propionate (SPDP) in order to incorporate TPA at the N-terminus of said peptide derived from the CD4 receptor of general sequence (III).

The molecular structure of SPDP is as follows:

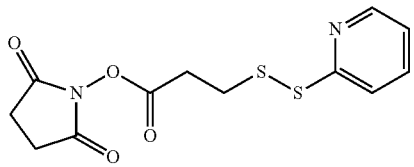 [SMILES: O=C(CCSSc1ccccn1)ON1C(=O)CCC1=O]

Moreover, as examples of active groups capable of coupling to an organic molecule by means of a covalent bond, the following groups can be cited: maleimide or bromoacetyl, S—S-pyridinium of thioacetyl.

When miniCD4 is activated by a protected thiol group (e.g. thioacetyl), it is possible to carry out coupling to an organic molecule which carries a maleimide group for example. This is possible when the functionalisation of the polyanionic polypeptide by a thiol group or protected thiol group, such as thioacetyl, poses a problem. This then called "reverse coupling".

Preferably, the active group is the maleimide group.

The molecular structure of the activated peptide according to the invention whose active group is maleimide is the following when SMPH is the bifunctional compound used:

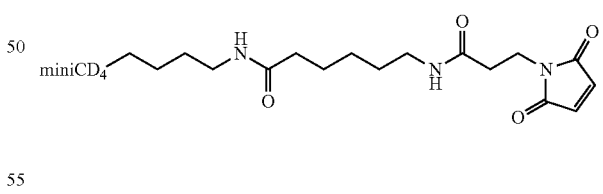

In this application, the term "SMPH activated miniCD4 peptide" refers to an activated peptide according to the invention whose amino acid Lys residue is covalently bound, advantageously by an amine bond, to a maleimide active group via a linker derived from SMPH.

According to another advantageous embodiment, the molecular structure of the activated peptide according to the invention whose active group is the maleimide group is the following when NHS-PEO$_2$-maleimide is the bifunctional compound used:

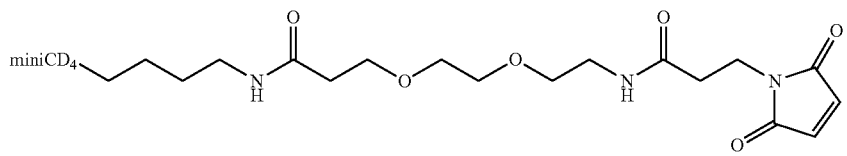

In this application, the term "maleimide activated miniCD4 peptide via a PEO$_2$ linker" refers to an activated peptide according to the invention whose amino acid Lys residue is covalently bound, advantageously by an amine bond, to a maleimide active group via a PEO$_2$ linker.

According to another preference, the active group is the thioacetyl group.

For example, the molecular structure of the activated peptide according to this invention whose active group is the thioacetyl group is the following when SATA is the bifunctional compound used:

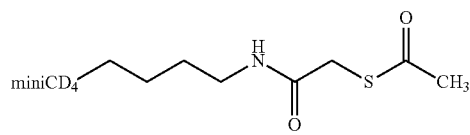

Similarly, the molecular structure of the activated peptide according to this invention whose active group is the thioacetyl group is the following when SATP is the bifunctional compound used:

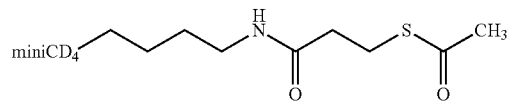

The thioacetyl group is a protected form of the thiol group. To deprotect the thiol group, we use hydroxylamine for example. This step is carried out simultaneously to coupling to the maleimide group carried by the organic molecule.

In this application, the terms "SATA activated miniCD4 peptide" and "SATP activated miniCD4 peptide" refer to an activated peptide according to the invention whose amino acid Lys residue is covalently bound, advantageously by an amine bond, to a protected thiol group (e.g. thioacetyl) via a linker derived from SATA or SATP.

Thus, according to a particular embodiment, the active group of the activated peptide is the maleimide group and the organic molecule carries a thiol or thioacetyl group.

The molecular structure of a conjugated molecule according to the invention, including a peptide derived from the CD4 receptor of general sequence (I) coupled to a modified anionic polypeptide (polyanion) carrying a thiol or protected thiol group, such as a thioacetyl group, is as follows when SMPH was used as bifunctional compound for the coupling:

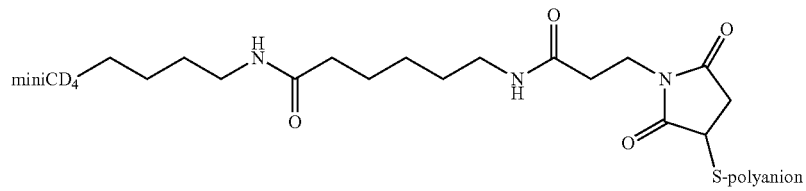

It can also be the following conjugated molecule when NHS-PEO$_2$-maleimide is the bifunctional compound used:

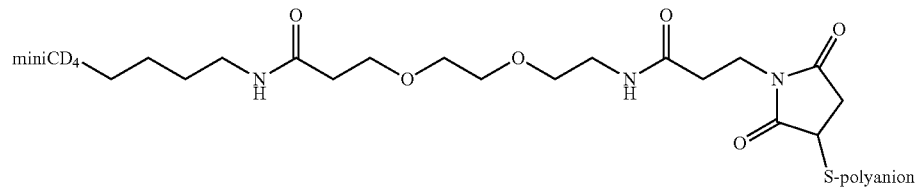

According to another embodiment, the conjugated molecule according to the invention comprises a peptide derived from the CD4 receptor comprising or consisting of general sequence (I), preferably sequence SEQ ID NO: 1, and an organic molecule carrying a maleimide or halogen group.

According to another particular embodiment, the active group of the activated peptide is the thioacetyl group and the organic molecule carries a maleimide or halogen group.

For example, the molecular structure of such a conjugated molecule including a peptide derived from the CD4 receptor of general sequence (I) coupled to an organic molecule carrying a maleimide group is as follows when SATA is used for the coupling:

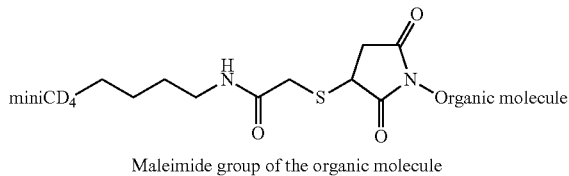

Maleimide group of the organic molecule

According to the invention, the anionic polypeptide (the organic molecule of the present invention) can be prepared by any convenient synthetic method known in the art. The operating conditions for the processes according to the invention for preparation of the activated peptide and conjugated molecule are well known to the person skilled in the art as illustrated in the following examples.

The examples and figures below illustrate the invention but do not limit its scope in any way.

FIGURE LEGENDS

FIG. 1 discloses the structure of the peptides of the invention.

Figure 1:
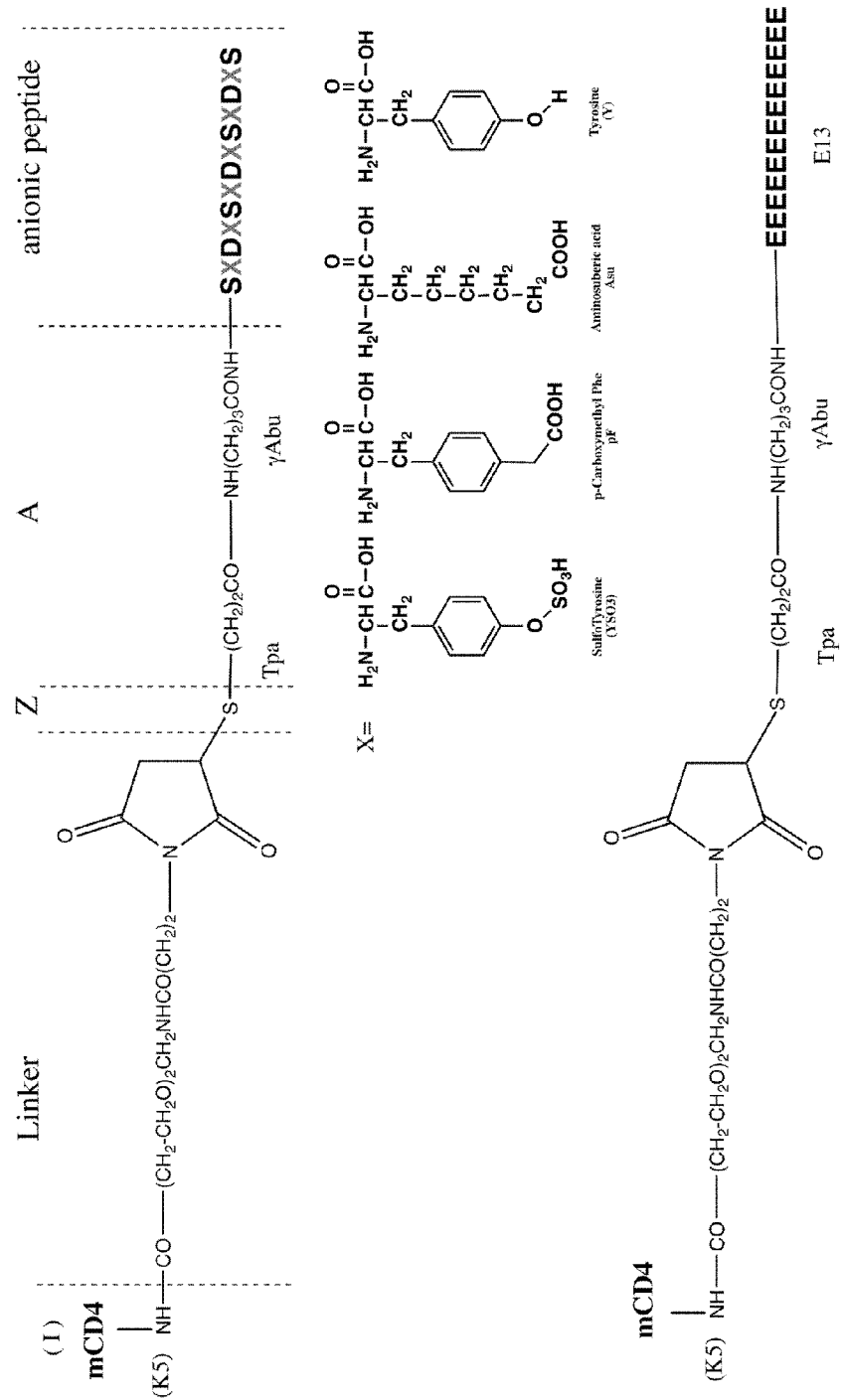
Figure 2:
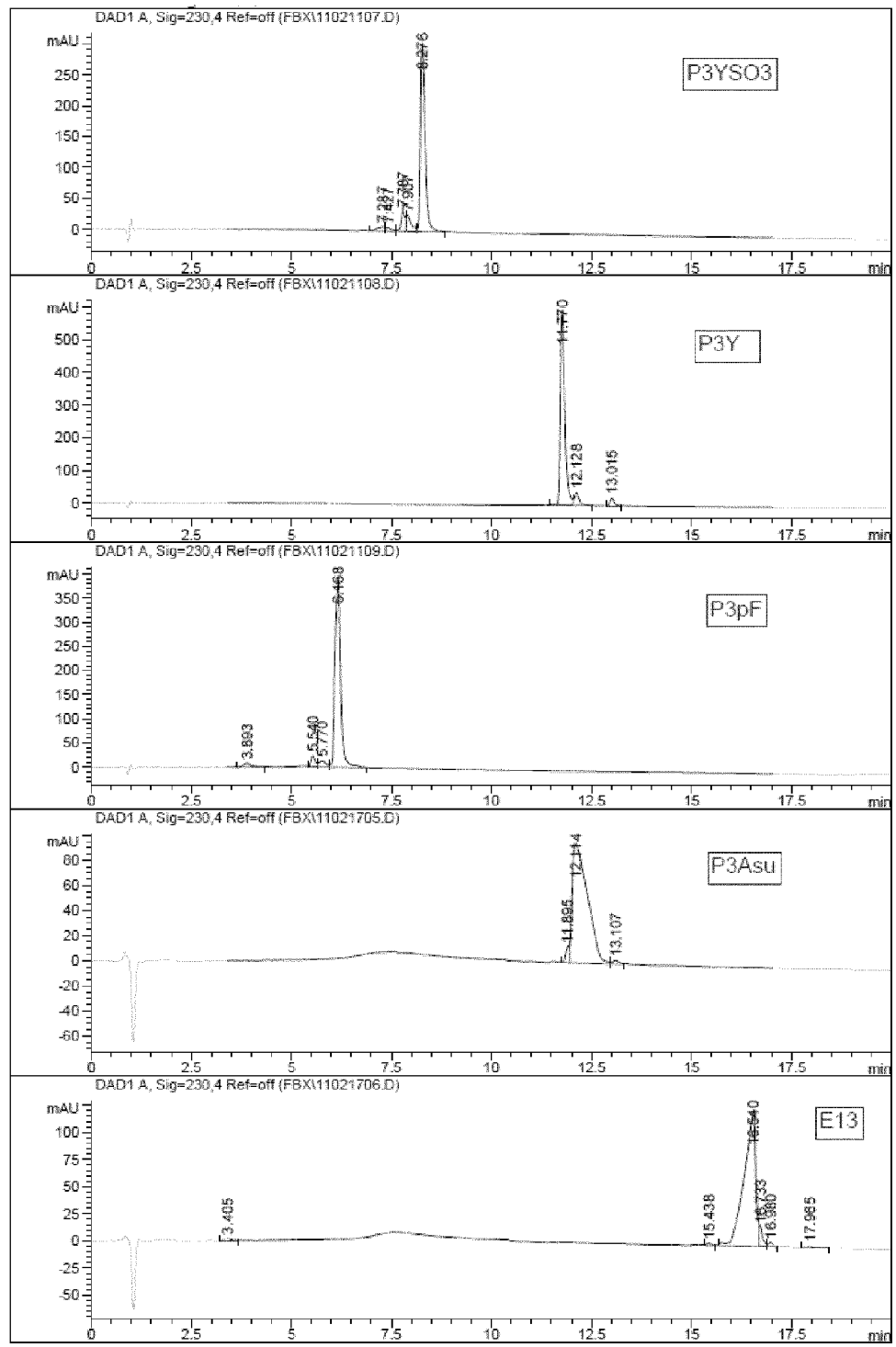
FIG. 2 represents the HPLC profile of the anionic polypeptide comprised in the conjugated molecules of the invention (from up to down: $P3Y_{SO3}$, P3Y, P3 pF, P3Asu, and E13).
Figure 3:
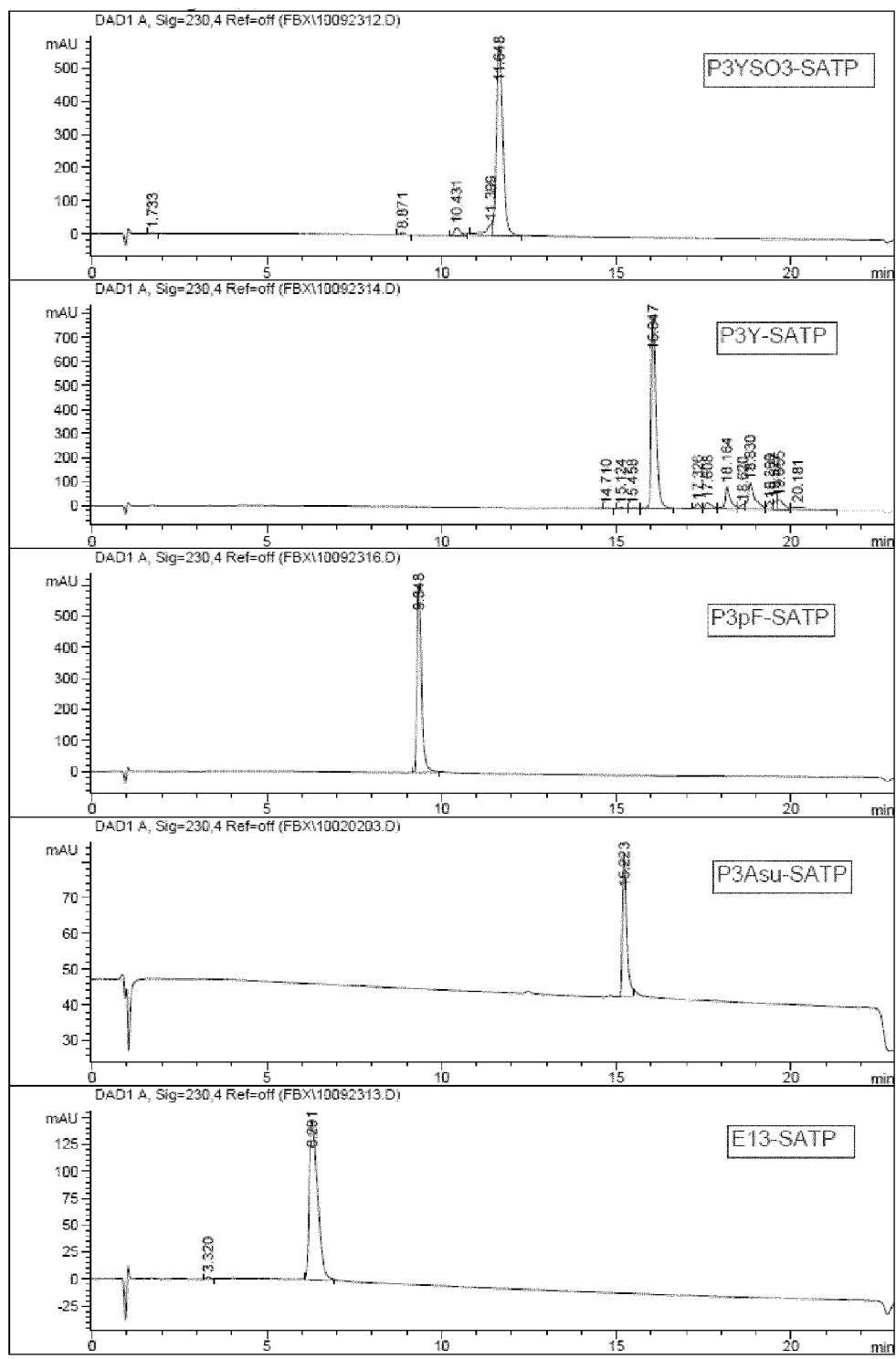
FIG. 3 represents the HPLC profile of the anionic polypeptide of the invention coupled to the S-acetylpropionate (SATP) group.
Figure 4:
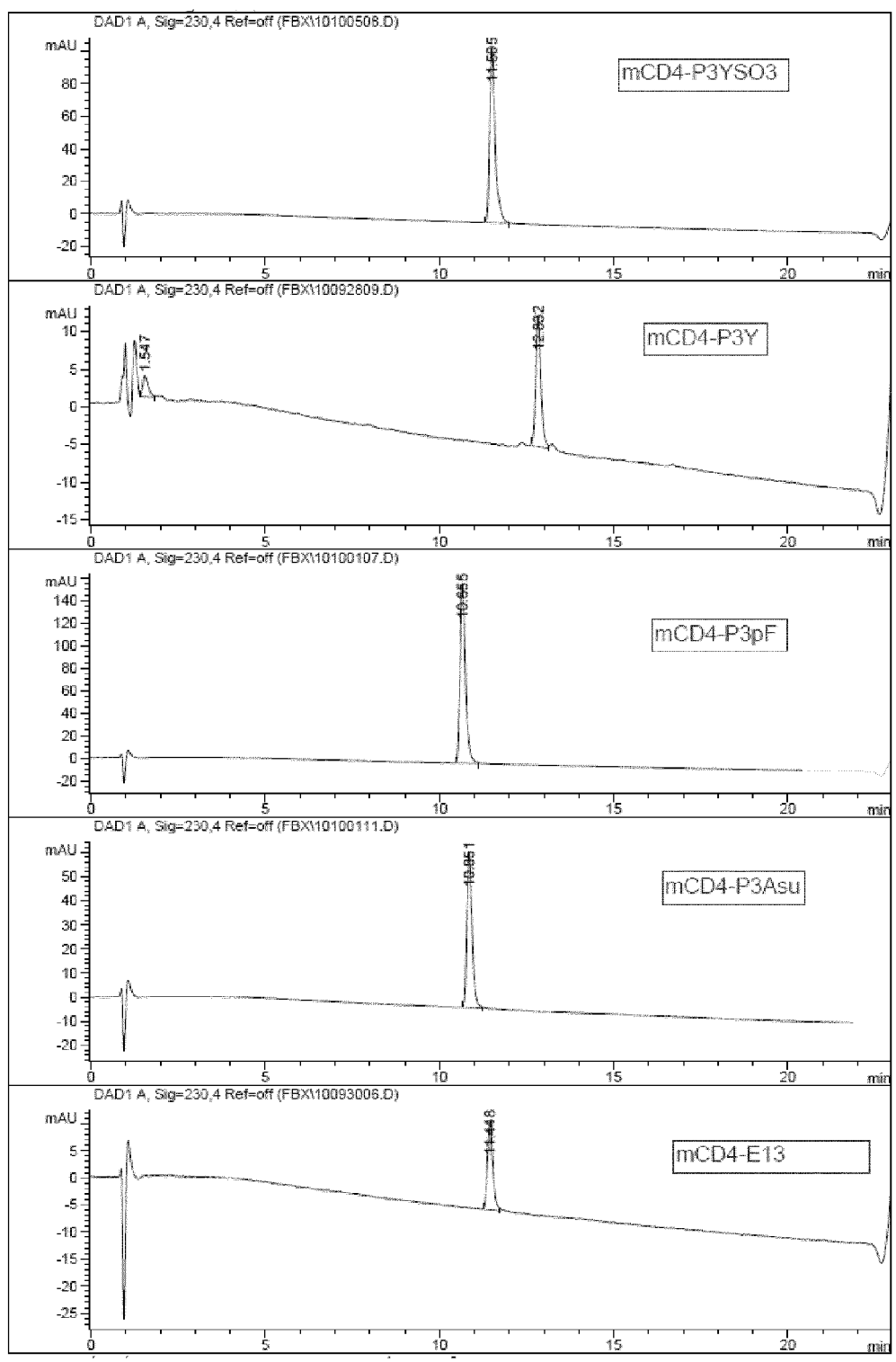
FIG. 4 represents the HPLC profile of the conjugated peptides of the invention.
Figure 5:
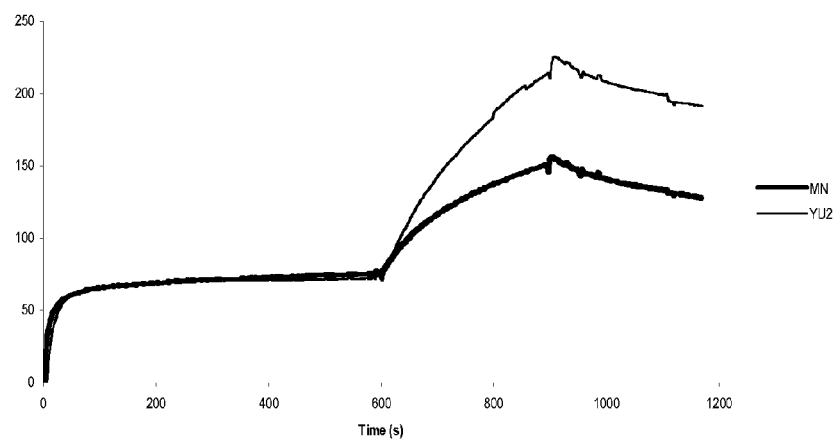
Figure 5:
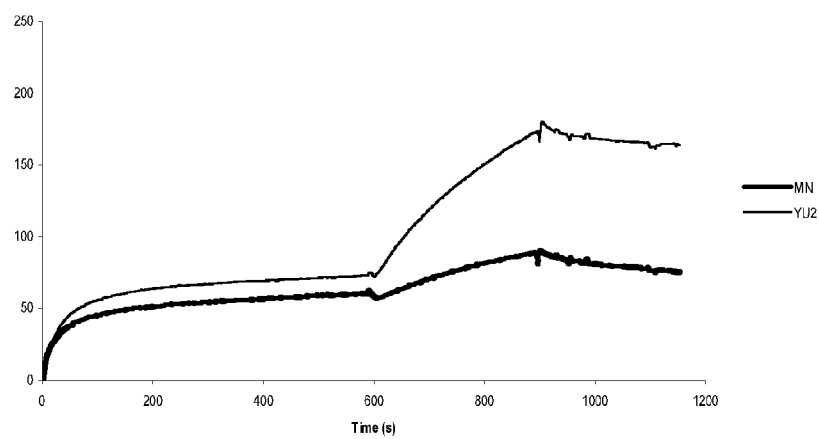
Figure 5:
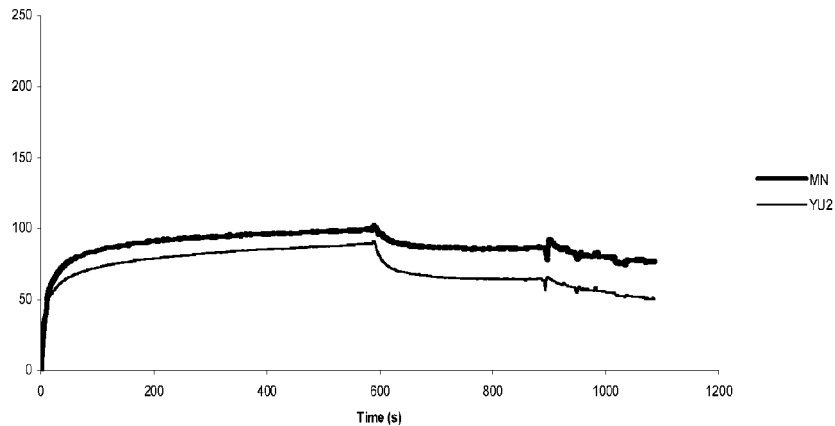
Figure 5:
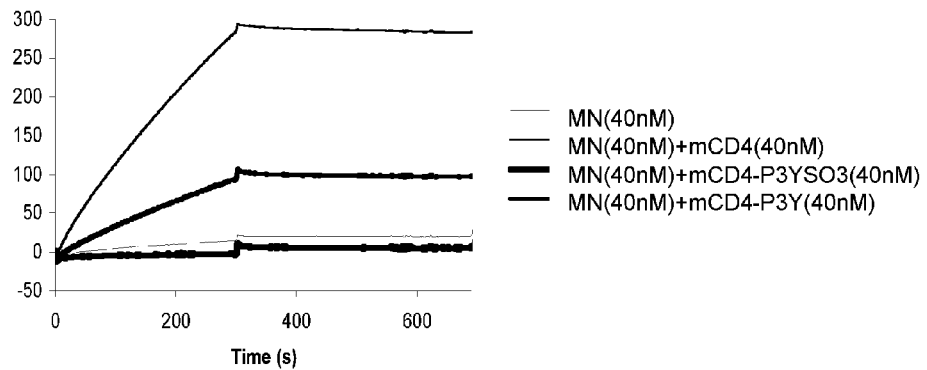
Figure 5:
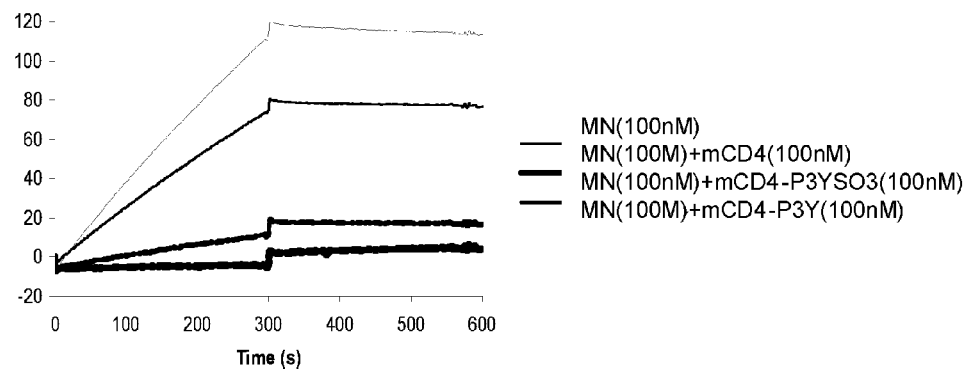
Figure 5:
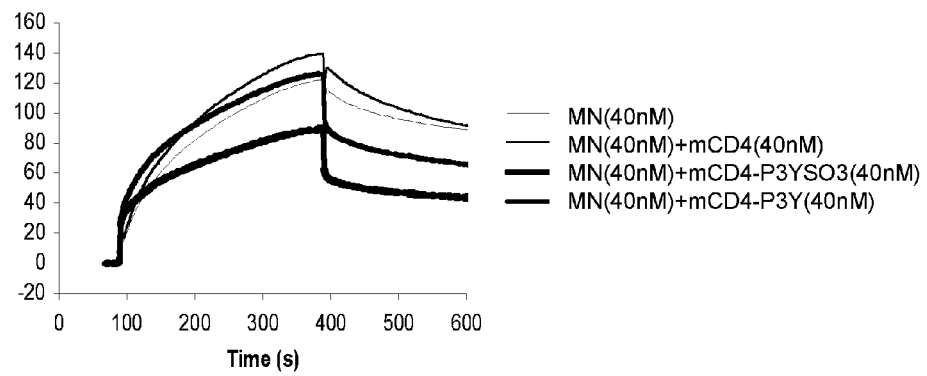
Figure 5:
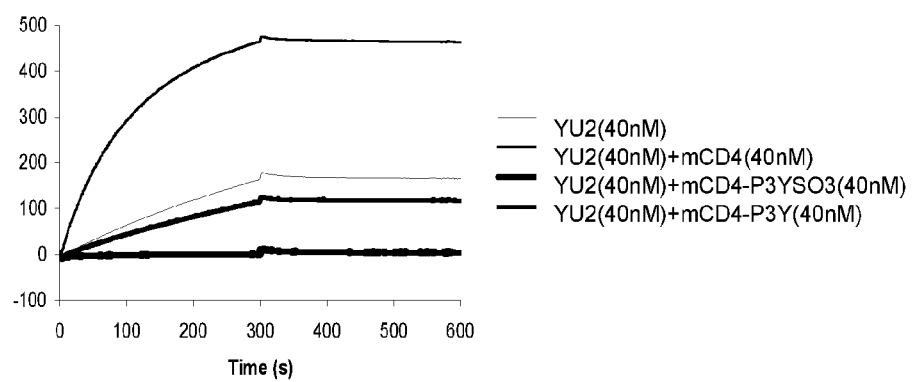
Figure 5:
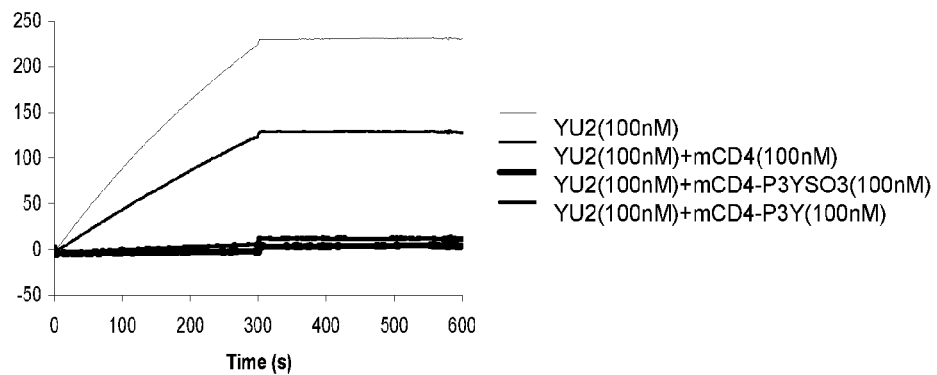

FIG. 5 represents the results of the binding assays performed by Surface Plasmon Resonance (SPR—Biacore) techniques, and showing the interaction between mAb17b (15 μg/ml) and surfaces coated with gp120 from X4 (MN) or R5 (YU2) virus, pretreated with 100 nM of: mCD4 alone(A), mCD4-P3Y(B) or mCD4-P3YSO3(C). When surfaces are coated with mAb17b (D and G), the interaction of gp120 from X4 (MN) or gp120 from R5 (YU2) depends on the presence of mCD4 (which induce the exposition of mAb17b epitope), but is fully inhibited when mCD4-P3Y or mCD4-P3YSO3 were used instead of mCD4. When surfaces are coated with sCD4 (E and H) the interactions are partially inhibited by mCD4 and fully inhibited by mCD4-P3Y or mCD4-P3YSO3. When surfaces are coated with heparin (F), the interaction is not inhibited by mCD4 and partially inhibited by mCD4-P3Y and mCD4-P3YSO3, the later being more active.

EXPERIMENTAL EXAMPLES

Example 1

Synthesis of the Conjugated Molecules of the Invention 1.1. Synthesis of the peptides of formula H-γ-Abu-SXDXSXDXSXDXS-OH with X=YSO3 (P3YSO3), Y (P3Y), Asu (P3Asu), or pF (P3 pF); H-γ-Abu-$SY_{SO3}DY_{SO3}SY_{SO3}$DYSYDYS-OH (Nter3Sulfates); H-γ-Abu-SYDYSYDY$_{SO3}$ $SY_{SO3}DY_{SO3}$S-OH (Cter3Sulfates); and H-γ-Abu-(Glu)$_{13}$-OH (E13); where γ-Abu: $NH_2$—$(CH_2)_3$—CO The following example describes the synthesis of modified peptides of formula H-γ-Abu-SXDXSXDXSXDXS-OH with X=$Y_{SO3}$ (P3YSO3), Y (P3Y), Asu (P3Asu), or pF (P3 pF); H-γ-Abu-$SY_{SO3}DY_{SO3}$ $SY_{SO3}$DYSYDYS-OH (Nter3 sulfates); H-γ-Abu-SYDYSYDY$_{SO3}SY_{SO3}DY_{SO3}$S—OH (Cter3sulfates); H-γ-Abu-(Glu)$_{13}$-OH (E13); where γ-Abu: $NH_2$—$(CH_2)_3$—CO. In this formula, the anionic peptide of the invention (except peptide E13) corresponds to SXDXSXDXSXDXS-OH (SEQ ID NO: 19), with X as above (identical or different).

The resulting modified peptides are:

```
P3YSO3 (SEQ ID NO: 14):
NH2-(CH2)3-CO-S-Y_SO3-D-Y_SO3-S-Y_SO3-D-Y_SO3-S-Y_SO3-
D-Y_SO3-S

P3Y (SEQ ID NO: 15):
NH2-(CH2)3-CO-S-Y-D-Y-S-Y-D-Y-S-Y-D-Y-S

P3pF (SEQ ID NO: 16):
NH2-(CH2)3-CO-S-pF-D-pF-S-pF-D-pF-S-pF-D-pF-S

P3 Asu (SEQ ID NO: 17):
NH2-(CH2)3-CO-S-Asu-D-Asu-S-Asu-D-Asu-F-Asu-F-D-
```

-continued

Asu-S

E13 (SEQ ID NO: 18):
NH$_2$-(CH$_2$)$_3$-CO-EEEEEEEEEEEE

Nter3sulfates (SEQ ID NO: 20):
NH2-(CH$_2$)$_3$-CO-S-Y$_{SO3}$-D-Y$_{SO3}$-S-Y$_{SO3}$-D-Y-S-Y-D-Y-S Cter3sulfates (SEQ ID NO: 21):
NH2-(CH$_2$)$_3$-CO-S-Y-D-Y-S-Y-D-Y$_{SO3}$-S-Y$_{SO3}$-D-Y$_{SO3}$-S Reagents Resins were purchased from RAPP Polymere GmbH. Fmoc AAs, HATU, NMP, DMF, TFA were from Applied Biosystems and Piperidin from Sigma. Fmoc-Tyr(SO3.NnBu4)-OH and Fmoc-γ-Aminobutyric-OH (γ-Abu) were from Novabiochem, (S)-Fmoc-2-amino-octanedioc acid-8-ter-butyl ester (Asu) from Polypeptides and Fmoc-L-4 (O-tButylcarboxymethyl)-Phe-OH (pF) from Anaspec. HPLC grade triethylamine acetate buffer was from GlenResearch. N-succinimidyl-5-acetylthiopropionate (SATP) was from Pierce.

General Protocol for Peptide Synthesis

Peptides were synthesized on H-Ser(tBu)-2-ClTrt-PS-resin (100 μmoles; 0.78 mmole/g) on an Applied 433 peptide synthesizer. E13 peptide was synthesized on Fmoc-Glu(tBu)-PHB-PS-resin (100 μmoles; 0.61 mmole/g). Chain elongation was performed using 10 equivalents of Fmoc amino acids and HATU/DIEA activation. Peptides were released from the resin by TFA/TIS/H2O (95/2.5/2.5) treatment for 1 h 30 at room temperature, except for sulphated peptides which was done at 4° C. (ice bath). The crude peptides were isolated by cold diethyl ether precipitation, solubilised in water by adding 3% NH$_4$OH, except the sulphated peptide that was rapidly dissolved in 100 mM ammonium hydrogen carbonate buffer. After lyophilisation, the crude peptides were purified by C18 RP-HPLC using 50 mM aqueous NEt3-AcOH (100 mM for the sulphated and E13 peptides) and CH$_3$CN as eluents. Purified peptides was checked by mass spectrometry (Waters ionspray Q-TOF-micro) and quantified by amino acids analyses (Hitachi L-8800 apparatus). Peptides purity was controlled by analytical C18 RP-HPLC using linear gradient of CH$_3$CN in 50 mM aqueous NEt3-AcOH over 20 min (Waters Symmetry C18-300 Å, 3.5 2.1×100 mm column, 0.35 ml/min flow rate).

TABLE 1 analysis of peptide purity by HPLC

| Peptide | Overall yield (%) | Formula | Expected mass (monoisotopic) | Found | HPLC retention time (min) |
|---|---|---|---|---|---|
| P3YSO3 | 4 | C$_{82}$H$_{98}$N$_{14}$O$_{49}$S$_6$ | 2253.3835 [M − H]$^-$ | 2253.3164 | 8.3 (10-30% over 20 min) |
| P3Y | 8 | C$_{82}$H$_{98}$N$_{14}$O$_{31}$ | 1775.6601 [M + H]$^+$ | 1775.6370 | 11.7 |
| P3pF | 14 | C$_{94}$H$_{110}$N$_{14}$O$_{37}$ | 2027.7235 [M + H]$^+$ | 2027.7490 | 6.2 |
| P3Asu | 10 | C$_{76}$H$_{122}$N$_{14}$O$_{37}$ | 1823.8174 [M + H]$^+$ | 1823.8474 | 16.5 (0-10% over 20 min) |
| E13 | 73 | C$_{69}$H$_{100}$N$_{14}$O$_{41}$ | 1781.6170 [M + H]$^+$ | 1781.6299 | 12.1 |
| Nter3 sulfates | 41 | C$_{82}$H$_{98}$N$_{14}$O$_{40}$S$_3$ | 2015.9495 M (average) | 2015.6544 | 12.242 (5-25% over 20 min) |
| Cter3 sulfates | 46 | C$_{82}$H$_{98}$N$_{14}$O$_{40}$S$_3$ | 2015.9495 M (average) | 2015.6346 | 12.454 (5-25% over 20 min) |

1.2. S-Acetylthiopropionate Peptides (SATP Peptides)

The peptides were dissolved in 100 mM sodium phosphate buffer pH 8.2 (1 mM final concentration). S-acetylthiopropionate group was introduced via stepwise addition of 10 equivalents of SATP (0.26 M in DMSO) over a 40 min period. After 1 h30, S-acetylthiopropionate peptides were purified by C18 RP-HPLC using linear gradient of CH$_3$CN in 50 mM aqueous NEt$_3$-AcOH over 20 min (C18-300 Å, 5 μm, 10×250 mm column, 6 ml/min flow rate). SATP derived peptides purity was controlled by analytical C18 RP-HPLC using linear gradient of CH$_3$CN in 50 mM aqueous NEt3-AcOH over 20 min (Waters Symmetry C18-300 Å, 3.5 μm, 2.1×100 mm column, 0.35 ml/min flow rate).

TABLE 2 analysis of the purity of the S-acetylthiopropionate peptides

| Peptide-SATP | Yield (%) | Formula | Expected mass (monoisotopic) | Found | HPLC retention time (min) (5-25% over 20 min) |
|---|---|---|---|---|---|
| P3YSO3-SATP | 60 | $C_{87}H_{104}N_{14}O_{51}S_7$ | 2383.3942 [M − H]⁻ | 2383.4316 | 11.6 |
| P3Y-SATP | 43 | $C_{87}H_{104}N_{14}O_{33}S_1$ | 1903.6533 [M − H]⁻ | 1903.6781 | 16.0 |
| P3pF-SATP | 50 | $C_{99}H_{116}N_{14}O_{39}S_1$ | 2155.7167 [M − H]⁻ | 2155.7869 | 9.3 |
| P3Asu-SATP | 36 | $C_{81}H_{128}N_{14}O_{39}S_1$ | 1953.8262 [M + H]⁺ | 1953.7822 | 15.2* |
| E13-SATP | 34 | $C_{74}H_{106}N_{14}O_{43}S_1$ | 1909.6181 [M − H]⁻ | 1909.6188 | 6.3 |
| Nter3 sulfates-SATP | 52 | $C_{87}H_{104}N_{14}O_{42}S_4$ | 2146.1159 M (average) | 2146.1746 | 11.0 (10-30% over 20 min) |
| Cter3 sulfates-SATP | 57 | $C_{87}H_{104}N_{14}O_{42}S_4$ | 2146.1159 M (average) | 2146.1357 | 11.3 (10-30% over 20 min) |

*10-30% linear gradient of $CH_3CN$ in 0.08% aqueous TFA over 20 min.

1.3. Maleimide Activated miniCD4 (mCD4-Mal)

The mini-CD4 peptide of the invention is obtained as disclosed in WO 2009/098147 and Nature Chemical Biology, 2009, 5(10), 743-748.

Mini-CD4-PEO2-maleimide=mini-CD4+linker

A solution of 10 mg of mCD4 (MW: 2897; 3.4 mmoles) in 1 ml of $H_2O$ was diluted in 1 ml of phosphate buffer 0.1 M pH 8. 4.5 mg of NHS-PEO₂-Maleimide (MW: 325; 13.8 mmoles; 4 equiv) were added to this cloudy solution in 20 μl of DMSO with stirring. After 10 minutes, 85% (HPLC) of the starting materials was converted into maleimide derivative. Because of the low stability of the maleimide group at pH 8, the coupling reaction was directly loaded onto a SepaK C18 column calibrated with 10% $CH_3CN$ in aqueous TFA 0.08%. The maleimide derivative was eluted with 50% $CH_3CN$. After freeze drying, the compound was then purified on a semi preparative column.

1.4. mCD4-Peptide Conjugates

SATP Peptides were dissolved in 100 mM sodium phosphate buffer pH 7.2 (1 mM final concentration). 100 equivalents of 0.5 M $NH_2OH$, HCl in 100 mM sodium phosphate buffer (pH adjusted to 7.2 by 4N NaOH) was added. Deprotection of the thiol function was monitored by HPLC. After 30 min, 0.3 equivalent of mCD4-Mal in $H_2O$ (1.5 mM) was added. After 30 min, mCD4-peptide conjugates were purified by C18 RP-HPLC using linear gradient of $CH_3CN$ in 50 mM aqueous NEt3-AcOH over 20 min (C18-300 Å, 5 μm, 10×250 mm column, 6 ml/min flow rate). mCD4-peptide conjugates were controlled by analytical C18 RP-HPLC using linear gradient of $CH_3CN$ in 50 mM aqueous NEt3-AcOH over 20 min (Waters Symmetry C18-300 Å, 3.5 μm, 2.1×100 mm column, 0.35 ml/min flow rate), negative mode mass spectrometry and quantified by amino acids analysis.

TABLE 3

HPLC analysis of the mCD4-peptide conjugates

| Conjugates | Yield (%) | Formula | Expected mass (average) | Found | HPLC retention time (min) (20-40% over 20 min) |
|---|---|---|---|---|---|
| mCD4-P3YSO3 | 47 | $C_{221}H_{314}N_{54}O_{88}S_{13}$ | 5552.0933 | 5551.5127 | 11.5 |
| mCD4-P3Y | 38 | $C_{221}H_{314}N_{54}O_{70}S_7$ | 5071.7081 | 5071.5005 | 12.8 |
| mCD4-P3pF | 67 | $C_{233}H_{326}N_{54}O_{76}S_7$ | 5323.9318 | 5323.5850 | 10.7 |
| mCD4-P3Asu | 23 | $C_{215}H_{338}N_{54}O_{76}S_7$ | 5119.8291 | 5119.5283 | 10.8 |
| mCD4-E13 | 58 | $C_{208}H_{316}N_{54}O_{80}S_7$ | 5077.5750 | 5077.1021 | 11.4 |
| mCD4-Nter3 sulfates | 36 | $C_{221}H_{314}N_{54}O_{79}S_{10}$ | 5311.9007 | 5311.5166 | 13.9 (20-35% over 20 min) |
| mCD4-Cter3 sulfates | 43 | $C_{221}H_{314}N_{54}O_{79}S_{10}$ | 5311.9007 | 5311.4155 | 14.0 (20-35% over 20 min) |

Synthesis of the control peptide mCD4-HS12 was performed as described in WO/2009/098147 and Nature Chemical Biology, 2009, 5(10), 743-748.

Example 2

Biacore Evaluation 2.1. Protocol

Two different gp120 were used, originating from a type X4 isolate (gp120 MN) and a type R5 isolate (gp120 YU2). The capacity of different molecules to inhibit gp120 interactions with various receptors or co-receptors is measured by surface plasmonic resonance (Biacore).

To do this, proteins (in this case gp120 envelop proteins) can be immobilized on the surface of a biosensor (Sensorchip CM 4 Biacore) in accordance with the described procedure (Vives et al. *J. Biol. Chem.* 279, 54327-54333, 2005). When injected on a surface coated with MN(X4) or YU2(R5) gp120 envelops, mCD4 binds and unmasks the CD4i epitope on gp120, responsible to envelop binding of mAb17b (FIG. 5A) (mAb17b antibody recognizes the epitope induced by CD4 and mimics co-receptor CCR5 or CXCR4). When mCD4 or the compound to be tested is injected onto these surfaces, the interaction signal between gp120 and mAb17b is measured as a function of time (FIGS. 5 A to C).

In another set of experiments, mAb17b are coated on the surface, and gp120 alone (grey line) or pre-incubated with mCD4, or the compound to be tested are injected onto these surfaces (FIGS. 5D and 5G). The interaction signal between gp120 and mAb17b is measured as a function of time.

In another set of experiments, sCD4 is coated on the surface, and gp120 alone (grey line) or pre-incubated with the compounds to be tested are injected onto these surfaces (FIGS. 5E and 5H). The interaction signal between gp120 and sCD4 is measured as a function of time.

In another set of experiments, heparin is coated on the surface, and gp120 alone (grey line) or pre-incubated with the compounds to be tested are injected onto these surfaces (FIG. 5F). The interaction signal between gp120 and heparin is measured as a function of time.

The difference between the light line and the heavy lines shows the inhibitory capacity of the tested compound vis-à-vis interactions between gp120 and the molecule immobilized on the biosensor.

2.2. Results mCD4-P3Y$_{SO3}$ Fully Inhibits mAb17b Binding on Gp120/mCD4 Complex.

When injected on gp120 surface coated with MN(X4) or YU2(R5) envelops, mCD4 binds and unmasks the CD4i epitope on gp120, responsible to envelop binding of mAb17b (FIG. 5A). The same experiments performed with mCD4-P3Y and mCD4-P3Y$_{SO3}$ (FIGS. 5B and 5C respectively) show that mCD4-P3Y partially inhibits mAb17b binding to MN(X4) (FIG. 5B), whereas mCD4-P3Y$_{SO3}$ fully inhibits mAb17b on MN(X4) and YU2(R5) (FIG. 5C).

mCD4-P3Y$_{SO3}$ Fully Inhibits MN(X4) Envelop Binding on mAb17b and CD4 and Partially on Heparin.

When injected on mAb 17b surface, MN envelop does not bind to 17b surface (CD4i epitope is masked, light line, FIG. 5D). This binding occurs when gp120 envelop is in complex with mCD4. When injected in complex with mCD4-P3Y$_{SO3}$, the binding is fully inhibited (FIG. 5D). MN envelop binds to CD4 surface. When injected in complex with mCD4-P3Y$_{SO3}$, the binding is fully inhibited (FIG. 5E), whereas MN binding to heparin is only partially inhibited by mCD4-P3Y$_{SO3}$ (FIG. 5F).

mCD4-P3Y$_{SO3}$ Fully Inhibits YU2(R5) Envelop Binding on mAb17b and CD4.

When injected on mAb17b surface, YU2 envelop partially binds to 17b surface. This binding is enhanced when mCD4/YU2 complex is injected. This binding is fully inhibited by mCD4-P3Y$_{SO3}$ (FIG. 5G). YU2 envelop binds to CD4 surface. When injected in complex with mCD4-P3Y$_{SO3}$, the binding is fully inhibited (FIG. 5H). As YU2 envelop does not bind to heparin surface, the experiment on heparin surface was not performed.

Example 3

Antiviral Activity of the Peptides of the Invention on the X4-Tropic HIV-1-LAI and R5-Tropic HIV-1/Ba-L Strains 3.1. Protocol The antiviral experiment have been performed as described in WO/2009/098147 and Nature Chemical Biology, 2009, 5(10), 743-748.

Briefly, the X4-tropic HIV-1-LAI (Barre-Sinoussi, Science 220, 868-71, 1983) or the R5-tropic HIV-1/Ba-L (Gartner et al, Science 233, 215-9, 1986) strains were amplified and titrated in vitro on Phytohemaglutinin-P (PHA-P)-activated peripheral blood mononuclear cells (PBMC). Tissue culture infectious doses were calculated using Kärber's formula (Kärber, Arch. Exp. Path. Pharmak. 162, 480-483, 1931). For the antiviral assay, PHA-P-activated PBMC were pre-treated for 30 minutes with six concentrations of each drug (1:5 dilutions between 0.5 µM and 160 pM) and infected with one hundred 50% tissue culture infectious doses (TCID50) of either the X4-tropic LAI or R5-tropic Ba-L strain. Drugs were maintained throughout the culture, and cell supernatants were collected at day 7 post-infection and stored at −20° C. Azidothymidine (AZT) was used in these experiments as an internal control. Viral replication was measured by quantifying reverse transcriptase (RT) activity in cell culture supernatants using the RetroSys HIV RT kit (Innovagen). In parallel, cytotoxicity of the samples was evaluated in uninfected PHA-P-activated PBMC by a methyltetrazolium salt (MTT) assay on day 7. Experiments were performed in triplicate and 50, 70 and 90% effective doses and cytotoxic doses were calculated using SoftMaxPro software.

PHA-P-activated PBMC were treated with each of the drug under investigation (1:5 dilutions between 0.5 µM and 160 µM) and infected with 100 TCID$_{50}$ of either HIV-1-LAI (X4 tropic) or /Ba-L (R5 tropic) strain. Molecules and viruses were maintained throughout the culture, and cell supernatants were collected at day 7 post-infection from which reverse transcriptase activity was quantified. Experiments were performed in triplicate and 50, 70 and 90% effective doses (ED), in nM (±S.D.) were calculated using SoftMaxPro software. None of these molecules showed cytotoxicity up to 1 µM.

3.2. Results

When used alone, none of the anionic peptides demonstrated antiviral activity at the highest concentration tested (500 nM). However, when conjugated to mCD4, they displayed inhibitory activity against the LAI and/or Ba-L strain, with effective doses giving 50% inhibition (EDO as low as 0.5 nM for mCD4-P3YSO₃, which compares well to 1.4 nM for mCD4-HS$_{12}$ (see table 4 below).

TABLE 4 anti-viral activity of the conjugated peptides of the invention (effective dose (ED, mean of triplicate determination), in nM (± s.d.), required to inhibit 50, 70 and 90% of HIV-1 replication)

|  |  | VIH-1-LAI(X4) |  | VIH-1/Ba-L(R5) |  |
|---|---|---|---|---|---|
|  |  | Average | ±S.D* | Average | ±S.D |
| P3YSO3 | ED50 | >500 | — | >500 | — |
|  | ED70 | >500 | — | >500 | — |
|  | ED90 | >500 | — | >500 | — |
| P3Y | ED50 | >500 | — | >500 | — |
|  | ED70 | >500 | — | >500 | — |
|  | ED90 | >500 | — | >500 | — |
| P3pF | ED50 | >500 | — | >500 | — |
|  | ED70 | >500 | — | >500 | — |
|  | ED90 | >500 | — | >500 | — |
| P3Asu | ED50 | >500 | — | >500 | — |
|  | ED70 | >500 | — | >500 | — |
|  | ED90 | >500 | — | >500 | — |
| E13 | ED50 | >500 | — | >500 | — |
|  | ED70 | >500 | — | >500 | — |
|  | ED90 | >500 | — | >500 | — |
| mCD4 | ED50 | 201 | 161 | >500 | — |
|  | ED70 | 242 | 169 | >500 | — |
|  | ED90 | 317 | 187 | >500 | — |
| mCD4P3YSO3 | ED50 | 0.5 | 0.2 | 1.3 | 1.1 |
|  | ED70 | 0.6 | 0.3 | 3.1 | 2.7 |
|  | ED90 | 1.1 | 0.8 | 20 | 9.2 |
| mCD4 P3Y | ED50 | 98 | 36 | 454 | 104 |
|  | ED70 | 124 | 74 | 498 | 11 |
|  | ED90 | 160 | 125 | >500 | — |
| mCD4 P3pF | ED50 | 8.2 | 6.5 | 245 | 196 |
|  | ED70 | 11 | 7.4 | >500 | — |
|  | ED90 | 20 | 11 | >500 | — |
| mCD4P3Asu | ED50 | 15 | 5 | 499 | 4.3 |
|  | ED70 | 20 | 7 | >500 | — |
|  | ED90 | 31 | 14 | >500 | — |
| mCD4 E13 | ED50 | 30 | 25 | 435 | 159 |
|  | ED70 | 36 | 31 | 451 | 121 |
|  | ED90 | 48 | 41 | >500 | — |
| mCD4-PEO2-HP12L | ED50 | 1.4 | 1.2 | 18 | 9.6 |
|  | ED70 | 1.7 | 1.6 | 215 | 231 |
|  | ED90 | 3.5 | 5.3 | >500 | — |
| AZT | ED50 | 11 | 6 | 8.7 | 7.0 |
|  | ED70 | 21 | 15 | 16 | 11 |
|  | ED90 | 60 | 53 | 38 | 28 |

*SD: standard deviation

None of these molecules showed cytotoxicity up to the highest tested dose (0.5 μM).

Example 4

Antiviral Activity of mCD4-P3YSO₃ on the 92UG029, SF162, 92US723, 96USHIPS4, 92HT599 and 98IN017 Strains 4.1. Protocol The antiviral assay was extended to a series of more clinically relevant primary strains, including 92UG029, SF162, 92US723, 96USHIPS4, 92HT599 and 98IN017.

Phytohemagglutinin (PHA)-P-activated PBMCs were infected either with the reference lymphotropic HIV-1/LAI strain (Barre-Sinoussi, et al., 1983) or with the reference macrophage-tropic HIV-1/Ba-L strain (Gartner, et al., 1986). These viruses were amplified in vitro with PHA-P-activated blood mononuclear cells. Viral stocks (including clinical isolates) were titrated using PHA-P-activated PBMCs, and 50% tissue culture infectious doses (TCID50) were calculated using Kärber's formula (Kärber, 1931). Viruses (125 TCID50) were incubated for 30 min with five concentrations (1:5 dilutions between 500 nM and 320 pM) of each of the molecules to be tested and added to 150 000 PBMCs (m.o.i.~0.001). Cell supernatants were collected at day 7 post-infection and stored at −20° C. In some cases, the compounds were added to the cells prior to viral challenge. Viral replication was measured by quantifying reverse transcriptase (RT) activity in the cell culture supernatants using the Lenti RT Activity Kit (Cavisi) and AZT was used as reference anti-HIV-1 molecule. In parallel, cytotoxicity was evaluated on day 7 in uninfected PHA-P-activated PBMC using a colorimetric methyl-tetrazolium salt (MTS/PMS) assay (Promega). Experiments were performed in triplicate and 50, 70 and 90% effective doses (ED) were calculated using SoftMaxPro software.

4.2. Results

As shown in Table 5 below, mCD4-P3YSO₃ displayed a high level of antiviral activity, characterized by $ED_{50}$ in the range of 0.2 to 1.2 nM for five of them, and 29 nM for HIV-1 98IN017, a Glade C virus. As for the LAI and Ba-L strains, the mCD4 or P3YSO₃ were only poorly active or inactive, further supporting the very strong synergistic effect induced by the coupling strategy. None of the molecules showed cytotoxicity at up to 1 μM.

TABLE 5 anti-HIV-1 activity of AZT, mCD4-P3YSO₃, P3YSO₃ and mCD4 against clinical HIV-1 isolates (effective dose (ED, mean of triplicate determination), in nM (±s.d.), required to inhibit 50, 70 and 90% of HIV-1 replication)

| Viral strain: Clade-tropism |  | 92UG029 A-X4 | SF162 B-R5 | 92US723 B-R5/X4 | 96USHIPS4 B-R5/X4 | 92HT599 B-X4 | 98IN017 C-X4 |
|---|---|---|---|---|---|---|---|
| AZT | $ED_{50}$ | 7 ± 0 | 8 ± 7 | 8 ± 0.1 | 19 ± 9 | 9 ± 4 | 8 ± 3 |
|  | $ED_{70}$ | 16 ± 3 | 13 ± 8 | 17 ± 1 | 27 ± 11 | 22 ± 5 | 19 ± 5 |
|  | $ED_{90}$ | 61 ± 17 | 31 ± 3 | 59 ± 19 | 56 ± 15 | 110 ± 13 | 108 ± 25 |
| mCD4-P3YSO₃ | $ED_{50}$ | 0.2 ± 0.0 | 0.3 ± 0.2 | 0.3 ± 0.1 | 1.2 ± 1 | 0.5 ± 0.2 | 29 ± 18 |
|  | $ED_{70}$ | 0.3 ± 0.1 | 0.4 ± 0.3 | 0.35 ± 0.2 | 1.6 ± 1.2 | 1.3 ± 0.9 | 147 ± 9 |
|  | $ED_{90}$ | 0.8 ± 0.3 | 0.9 ± 0.2 | 0.45 ± 0.2 | 3 ± 1.4 | 3.5 ± 0.0 | >500 |
| P3YSO₃ | $ED_{50}$ | >500 | >500 | >500 | >500 | >500 | >500 |
|  | $ED_{70}$ | >500 | >500 | >500 | >500 | >500 | >500 |
|  | $ED_{90}$ | >500 | >500 | >500 | >500 | >500 | >500 |
| mCD4 | $ED_{50}$ | 403 ± 76 | 245 ± 155 | 23 ± 1 | >500 | 355 ± 155 | >500 |
|  | $ED_{70}$ | >500 | 352 ± 105 | 34 ± 10 | >500 | >500 | >500 |
|  | $ED_{90}$ | >500 | >500 | 52 ± 22 | >500 | >500 | >500 |

We also observed that mCD4-P3YSO3 does not need to be preincubated with the virus to be active. Indeed, addition of the molecule either to the cells, prior to the viral challenge or to the virus prior to the cell infection return, identical results (cf. table 7).

TABLE 7

Anti-HIV-1 activity of AZT, mCD4-P3YSO3, P3YSO3 and mCD4 against LAI HIV-1 (effective dose (ED, mean of triplicate determinations), in nM (±s.d.) required to inhibit 50, 70 and 90% of HIV-1 replication, when the compounds were preincubated either with the cells or with the viruses)

|  |  | Pre-treated cells | Pre-treated viruses |
|---|---|---|---|
| AZT | $ED_{50}$ | 16.5 ± 12 | 20 ± 12 |
|  | $ED_{70}$ | 33 ± 18 | 38 ± 18 |
|  | $ED_{90}$ | 96 ± 11 | 111 ± 40 |
| mCD4-P3YSO3 | $ED_{50}$ | 0.5 ± 0.2 | 0.5 ± 0.3 |
|  | $ED_{70}$ | 0.6 ± 0.2 | 0.7 ± 0.3 |
|  | $ED_{90}$ | 1 ± 0.2 | 0.9 ± 0.2 |
| P3YSO3 | $ED_{50}$ | >500 | >500 |
|  | $ED_{70}$ | >500 | >500 |
|  | $ED_{90}$ | >500 | >500 |
| mCD4 | $ED_{50}$ | 310 ± 190 | 406 ± 94 |
|  | $ED_{70}$ | >500 | 474 ± 27 |
|  | $ED_{90}$ | >500 | >500 |

Example 5

Antiviral Activity of mCD4-P3YSO$_3$ in Cellulo on SHIVsf162p3 Cells 5.1. Protocol TZN-bl cells that express Luceriferase under the control of the HIV LTR were used. These cells express high levels of CD4 and CCR5 and can be easily infected with HIV-1/-2 and SIV. Upon infection of these cells, viral Tat will induce transcription of Luciferase. The Luc signal is proportional to the amount of infection. We add a serial dilution of the compound to be tested (mCD4, mCD4-HS12 or mCD4-P3YSO$_3$) to cells and subsequently add virus. The obtained Luc signal is read out after 48 h.

The test was carried out in duplicate.

5.2. Results

The results obtained are presented in the table 6 below.

|  | EC50 (nM) | |
|---|---|---|
|  | 1$^{st}$ experiment | 2$^{nd}$ experiment |
| mCD4 | 4617 | 6126 |
| mCD4-HS12 | 781 | 631 |
| mCD4-P3YSO$_3$ | 34 | 37 |

CONCLUSIONS

This study thus shows that relatively small synthetic molecules, comprising a 3 kDa CD4 mimetic linked to an anionic polypeptide can efficiently mimic several large gp120 ligands, including CD4 and coreceptor binding site recognizing mAbs. Remarkably, the conjugates described in the present invention neutralize both R5- and X4-tropic HIV-1, a significant advantage since the efficacy of CCR5-specific antagonists could be jeopardized by the emergence of viral strains that utilize CXCR4, for which no inhibitors are yet available.

Surprisingly, the peptides of the invention displayed a better antiviral activity than the molecules of the prior art (mCD4-HS12) both on X4 and R5 virus strains and can thus enhance the inhibition of the HIV virus entry into host cells.

The conjugated molecule mCD4-P3Y$_{SO3}$ has far better inhibitory effect than any other tested compounds (ED50 of 0.5 and 1.3 against respectively X4 and R5).

ABBREVIATIONS

Fmoc: 9-fluorenylmethyloxycarbonyl
DMF: Dimethylformamide
HATU: hexafluorophosphate N-oxide of N[(dimethylamino)-1H-1,2,3-triazolo[4,5-b]pyridine-1-ylmethylene]-N-methylmethanaminium
DIEA: diisopropylethylamine
SPDP: N-succinimidyl-3(2-pyridyldithio)propionate
TFA: trifluoroacetic acid
EDT: ethanedithiol
TIS: triisopropylsilane
DTT: 1,4-dithiothreitol
MPLC: medium pressure liquid chromatography
ES$^+$MS: electrospray mass spectrometry, positive mode
GSH: reduced glutathion
GSSG: oxidised glutathion
HPLC: high-performance liquid chromatography
RP-HPLC: reverse phase high-performance liquid chromatography
SMPH: succinimidyl-6[β-maleimidopropionamido]hexanoate
SATP: N-succinimidyl-5-acetylthioproprionate
RT: room temperature
Rt: retention time
Cbz: benzyloxycarbonyl
pMBn: p-methoxybenzyl
Bn: benzyl
Ac: acetyl
Me: methyl
Et: ethyl
eq: equivalent
HRMS: high resolution mass spectrum
ESI: electrospray ionisation
LC-ESI-TOF-MS: Liquid chromatography/electrospray ionization Time-of-Flight mass spectrometry
LCMS: Liquid chromatography/Mass spectrometry
DMSO: Dimethylsulfoxide

The invention claimed is:

1. A conjugated molecule comprising a peptide derived from the CD4 receptor, said peptide being coupled to an organic molecule by means of a linker, wherein:

the said peptide derived from the CD4 receptor comprises the following general sequence (I):

(I)
Xaa$^f$ - P1- Lys - Cys - P2 - Cys - P3 - Cys - Xaa$^g$ - Xaa$^h$ - Xaa$^i$ - Xaa$^j$ - Cys - Xaa$^k$ - Cys - Xaa$^l$ - Xaa$^m$, in which:
P1 represents 3 to 6 amino acid residues,
P2 represents 2 to 4 amino acid residues,
P3 represents 6 to 10 amino acid residues,
Xaa$^f$ represents N-acetylcysteine (Ac-Cys) or thiopropionic acid (TPA),
Xaa$^g$ represents Ala or Gln,
Xaa$^h$ represents Gly or (D)Asp or Ser,
Xaa$^i$ represents Ser or His or Asn,
Xaa$^j$ represents biphenylalanine (Bip), phenylalanine or [beta]-naphthylalanine,
Xaa$^k$ represents Thr or Ala,
Xaa$^l$ represents Gly, Val or Leu, and
Xaa$^m$ represents —NH$_2$ or —OH, the amino acid residues in P1, P2 and P3 being natural or non-natural, identical or different, said residues of P1, P2 and P3 being all different from the Lys residue and P1, P2 and P3 having a sequence in common or not, and the said organic molecule comprises
an anionic polypeptide having a sequence of S-(X-D-X-S)$_n$, where n represents an integer between 1 and 5, S represents serine and D aspartic acid, and X is selected from the group consisting of: tyrosine, sulfotyrosine, tyrosine sulfonate, aminosuberic acid, and p-carboxymethyl phenylalanine, and where the various X groups are identical or different, a molecular group A-Z, wherein:
A comprises a group chosen between the groups of formula —CO(CH2)$_3$NH—CO(CH$_2$)$_2$—, —CO(CH$_2$)$_p$—NH—CO—(CH$_2$)$_q$—, —CO(CH$_2$—CH$_2$)—(O—CH$_2$—CH$_2$)$_p$—NH—CO—(CH$_2$)$_q$—, —CO(CH$_2$)$_p$—NH—CO—(CH$_2$—CH$_2$—O)$_q$—(CH$_2$—CH$_2$)— and —CO(CH$_2$—CH$_2$)—(O—CH$_2$—CH$_2$)$_p$—NH—CO—(CH$_2$—CH$_2$—O)$_q$—(CH$_2$—CH$_2$)—, wherein p represents an integer between 1 and 10 and q represents an integer between 1 and 10, and wherein the first carbonyl group is coupled to the N-terminal end of the anionic polypeptide, and
Z represents a halogen atom, a thiol or a maleimide group, the said anionic polypeptide being linked to the linker by the said molecular group of formula A-Z, the linker resulting from the coupling of a bifunctional compound respectively with the peptide derived from the CD4 receptor and the organic molecule, the said bifunctional compound incorporating two active groups wherein one of the two active groups is capable of forming a covalent bond with the free amino group (—NH$_2$) of the residue of the amino acid Lys present in general sequence (I) and the other active group is a halogen atom or a maleimide group when Z is a thiol or a protective thiol group when Z is a halogen atom or a maleimide group.

2. The conjugated molecule according to claim 1, wherein the sequence of the peptide derived from the CD4 receptor of general sequence (I) is chosen from the group consisting of sequences SEQ ID NO: 1 and SEQ ID NO: 2.

3. The conjugated molecule according to claim 1, wherein the linker is chosen from the group consisting of: CO—(CH$_2$O)$_2$CH$_2$NHCO(CH$_2$)$_2$ pyrrolidinyl-2,5-dione with k representing an integer comprised between 2 and 24, with k1 representing an integer equal to 1, 2, 3, 5 and 10, -continued

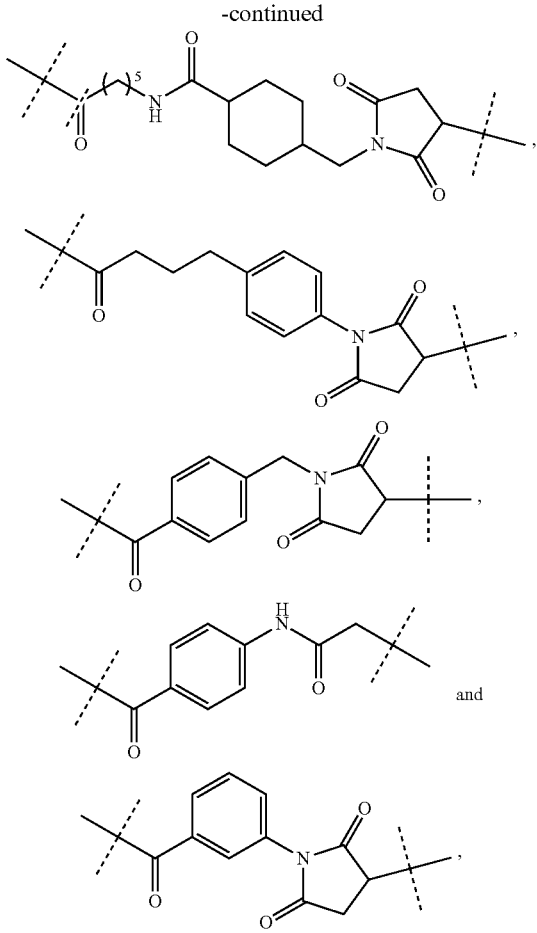

when Z represents a thiol group, and among:

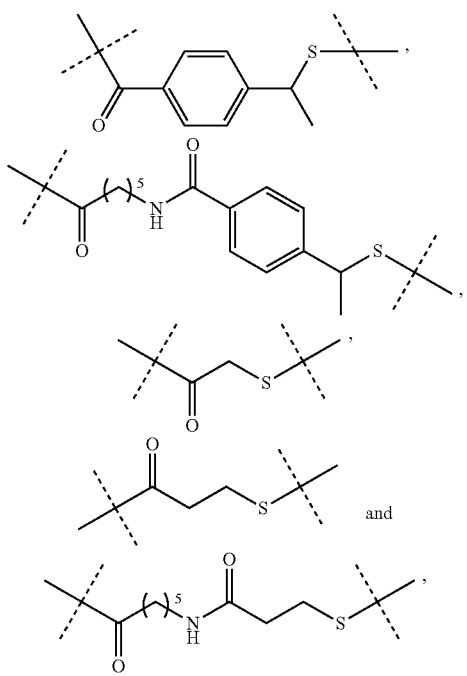

4. The conjugated molecule according to claim 1, wherein the anionic polypeptide consists of 13 amino acids.

5. The conjugated molecule according to claim 1, wherein X is sulfotyrosine.

6. The conjugated molecule according to claim 1, wherein said anionic polypeptide has a sequence which is selected from the group consisting of: S-(Y-D-Y-S)$_n$, S-(Y$_{SO3}$-D-Y$_{SO3}$-S)$_n$, S-(Y$_{SN}$-D-Y$_{SN}$-S)$_n$, S(pF-D-pF-S)$_n$, and S-(Asu-D-Asu-S)n, where n represents an integer between 1 and 5, S represents serine, D represents aspartic acid, Y represents tyrosine, Y$_{SO3}$ represents sulfotyrosine, Y$_{SN}$ represents tyrosine sulfonate, pF represents p-carboxymethyl phenylalanine and Asu represents aminosuberic acid.

7. The conjugated molecule according to claim 1, wherein said anionic polypeptide has a sequence which is selected from the group consisting of: S-Y-D-Y-S-Y-D-Y-S-Y-D-Y-S (SEQ ID NO: 8), S-Y$_{SO3}$-D-Y$_{SO3}$-S-Y$_{SO3}$-D-Y$_{SO3}$-S-Y$_{SO3}$-D-Y$_{SO3}$-S (SEQ ID NO: 4), S-Y$_{SN}$-D-Y$_{SN}$-S-Y$_{SN}$-D-Y$_{SN}$-S-Y$_{SN}$-D-Y$_{SN}$-S (SEQ ID NO: 5), S-pF-D-pF-S-pF-D-pF-S-pF-D-pF-S (SEQ ID NO: 6), S-Asu-D-Asu-S-Asu-D-Asu-F-Asu-F-D-Asu-S (SEQ ID NO: 7), S-Y$_{SO3}$-D-Y$_{SO3}$-S-Y$_{SO3}$-D-Y-S-Y-D-Y-S (SEQ ID NO: 20), and S-Y-D-Y-S-Y-D-Y$_{SO3}$-S-Y$_{SO3}$-D-Y$_{SO3}$-S (SEQ ID NO: 21), where S represents serine, D represents aspartic acid, Y represents tyrosine, Y$_{SO3}$ represents sulfotyrosine, Y$_{SN}$ represents tyrosine sulfonate, pF represents p-carboxymethyl phenylalanine and Asu represents aminosuberic acid.

8. The conjugated molecule according to claim 1, wherein:
the peptide derived from the CD4 receptor is chosen from the group consisting of sequences SEQ ID NO: 1 and SEQ ID NO: 2,
the linker is CO—(CH$_2$CH$_2$O)$_2$CH$_2$CH$_2$NHCO(CH$_2$)$_2$pyrrolidinyl-2,5-dione,
the organic molecule comprises an anionic polypeptide having the following sequence S-Y$_{SO3}$-D-Y$_{SO3}$-S-Y$_{SO3}$-D-Y$_{SO3}$-S-Y$_{SO3}$-D-Y$_{SO3}$-S (SEQ ID NO: 4) where S represents serine, D represents aspartic acid, and Y$_{SO3}$ represents sulfotyrosine, which is linked to the linker by a molecular group of formula A-Z, wherein A is —CO(CH$_2$)$_3$NH—CO(CH$_2$)$_2$— and Z is a thiol group.

9. The conjugated molecule according to claim 1, wherein A represents a group of formula —CO(CH$_2$)NH—CO(CH$_2$)$_2$—.

10. The conjugated molecule according to claim 1, wherein said anionic polypeptide has a sequence of S-X-D-X-S-X-D-X-S-X-D-X-S (SEQ ID NO: 19).

11. The conjugated molecule according to claim 1, wherein the various X groups of the anionic polypeptide are identical.

12. A pharmaceutical composition comprising a conjugated molecule according to claim 1 and a pharmaceutically acceptable vehicle.

13. A process for the preparation of a conjugated molecule according to claim 1, comprising the following steps:
a. contacting the peptide derived from the CD4 receptor of general sequence (I) as defined in claim 1 with a bifunctional compound carrying two active groups, so that one of the two active groups forms a covalent bond with the free amino group (—NH$_2$) of the residue of the amino acid Lys present in general sequence (I), in order to obtain an activated peptide carrying the second active group of the bifunctional group and
b. contacting the activated peptide obtained at step (a) with an organic molecule carrying a functional group as defined in claim 1 or with an organic molecule corresponding to the organic molecule carrying a thiol group defined in claim 1 for which the thiol group (SH) has been protected by a protective thiol group, so that the active group of the activated peptide forms a covalent bond with the functional group, protected or not, of the organic molecule, in order to obtain the conjugated molecule.

14. A method for treating AIDS comprising the administration to a person in need thereof of an effective amount of a conjugated molecule according to claim 1.

* * * * *

UNITED STATES PATENT AND TRADEMARK OFFICE
CERTIFICATE OF CORRECTION

PATENT NO. : 9,078,928 B2
APPLICATION NO. : 14/005688
DATED : July 14, 2015
INVENTOR(S) : Baleux et al.

Page 1 of 2

It is certified that error appears in the above-identified patent and that said Letters Patent is hereby corrected as shown below:

In the Specification

Column 3, Line 44, "CH$_2$-CH$_2$)–NH-CO–(CH$_2$–CH$_2$)–(O)$q$-" should read -- CH$_2$-CH$_2$)$_p$–NH–CO–(CH$_2$–CH$_2$)–(O)$q$- --.

Column 8, Line 39, "3,4-difluoropheny 1 alanine" should read -- 3,4-difluorophenyl alanine --.

Column 11, Lines 8-9, "S-(Y$_{SO3}$-D-Y$_{SO3}$-S)$_n$, S-(Y$_{SN}$-D-Y$_{SN}$-S)-S-(pF-D-pF-S)-S-(Asu-D-Asu-S)$_n$" should read -- S-(Y$_{SO3}$-D-Y$_{SO3}$-S)$_n$, S-(Y$_{SN}$-D-Y$_{SN}$-S)$_n$, S-(pF-D-pF-S)$_n$, S-(Asu-D-Asu-S)$_n$ --.

Column 14, Line 11, "(N-succinimidyl-5-acetylthioacetate)" should read -- (N-succinimidyl-S-acetylthioacetate) --.

Column 15, Line 31, "N-succinimidyl-5-acetylthioacetate" should read -- N-succinimidyl-S-acetylthioacetate --.

Column 15, Lines 32-33, "N-succinimidyl-5-acetylthioproprionate" should read -- N-succinimidyl-S-acetylthioproprionate --.

Column 15, Line 60, "(Rockford, Ill.)" should read -- (Rockford, IL) --.

In the Claims

Claim 1, Column 46, Line 14, "Z is a thiol or a protective" should read -- Z is a thiol group or is a thiol or a protective --.

Signed and Sealed this
Twenty-ninth Day of September, 2020

Andrei Iancu
*Director of the United States Patent and Trademark Office*

CERTIFICATE OF CORRECTION (continued)
U.S. Pat. No. 9,078,928 B2

Claim 3, Column 47, Line 20, the third formula: " 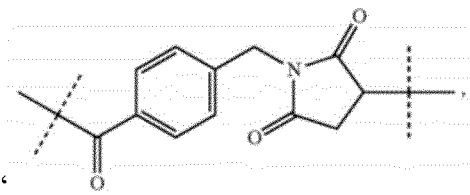 " should read as -- 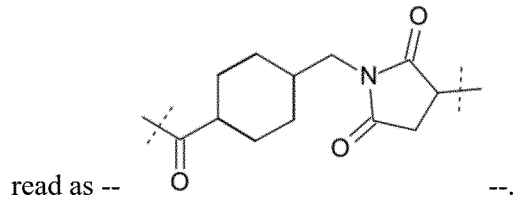 --.

Claim 3, Column 47, Line 65, at the end of the claim before the ".", insert -- when Z represents a maleimide group or a halogen atom --.

Claim 8, Column 48, Line 33, "CH₂" should read -- $CH_2$ --.

Claim 9, Column 48, Line 43, "–CO(CH₂)NH-CO" should read -- $-CO(CH_2)_3NH-CO$ --.

SEQUENCE LISTING

<160> NUMBER OF SEQ ID NOS: 21

<210> SEQ ID NO 1
<211> LENGTH: 26
<212> TYPE: PRT

```
<213> ORGANISM: artificial
<220> FEATURE:
<223> OTHER INFORMATION: CD4 derived peptide
<220> FEATURE:
<221> NAME/KEY: MOD_RES
<222> LOCATION: (1)..(1)
<223> OTHER INFORMATION: TPA-Asn
<220> FEATURE:
<221> NAME/KEY: misc_feature
<222> LOCATION: (22)..(22)
<223> OTHER INFORMATION: Xaa represents a Bi-phenylalanine
<220> FEATURE:
<221> NAME/KEY: MOD_RES
<222> LOCATION: (26)..(26)
<223> OTHER INFORMATION: Val-NH2

<400> SEQUENCE: 1

Asn Leu His Lys Cys Gln Leu Arg Cys Ser Ser Leu Gly Leu Leu Gly
1               5                   10                  15

Arg Cys Ala Gly Ser Xaa Cys Ala Cys Val
            20                  25

<210> SEQ ID NO 2
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: MOD_RES
<222> LOCATION: (1)..(1)
<223> OTHER INFORMATION: TPA-Asn
<220> FEATURE:
<221> NAME/KEY: misc_feature
<222> LOCATION: (22)..(22)
<223> OTHER INFORMATION: Xaa represents a Bi-phenylalanine

<400> SEQUENCE: 2

Asn Leu His Lys Cys Gln Leu Arg Cys Ser Ser Leu Gly Leu Leu Gly
1               5                   10                  15

Arg Cys Ala Gly Ser Xaa Cys Ala Cys Val
            20                  25

<210> SEQ ID NO 3
<211> LENGTH: 13
<212> TYPE: PRT
<213> ORGANISM: artificial
<220> FEATURE:
<223> OTHER INFORMATION: artificial peptide

<400> SEQUENCE: 3

Glu Glu Glu Glu Glu Glu Glu Glu Glu Glu Glu Glu Glu
1               5                   10

<210> SEQ ID NO 4
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (2)..(2)
<223> OTHER INFORMATION: Xaa represents a sulfo tyrosine
<220> FEATURE:
<221> NAME/KEY: misc_feature
<222> LOCATION: (4)..(4)
<223> OTHER INFORMATION: Xaa represents a sulfo tyrosine
<220> FEATURE:
<221> NAME/KEY: misc_feature
<222> LOCATION: (6)..(6)
```

```
<223> OTHER INFORMATION: Xaa represents a sulfo tyrosine
<220> FEATURE:
<221> NAME/KEY: misc_feature
<222> LOCATION: (8)..(8)
<223> OTHER INFORMATION: Xaa represents a sulfo tyrosine
<220> FEATURE:
<221> NAME/KEY: misc_feature
<222> LOCATION: (10)..(10)
<223> OTHER INFORMATION: Xaa represents a sulfo tyrosine
<220> FEATURE:
<221> NAME/KEY: misc_feature
<222> LOCATION: (12)..(12)
<223> OTHER INFORMATION: Xaa represents a sulfo tyrosine

<400> SEQUENCE: 4

Ser Xaa Asp Xaa Ser Xaa Asp Xaa Ser Xaa Asp Xaa Ser
1               5                   10

<210> SEQ ID NO 5
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (2)..(2)
<223> OTHER INFORMATION: Xaa represents a tyrosine sulfonate
<220> FEATURE:
<221> NAME/KEY: misc_feature
<222> LOCATION: (4)..(4)
<223> OTHER INFORMATION: Xaa represents a tyrosine sulfonate
<220> FEATURE:
<221> NAME/KEY: misc_feature
<222> LOCATION: (6)..(6)
<223> OTHER INFORMATION: Xaa represents a tyrosine sulfonate
<220> FEATURE:
<221> NAME/KEY: misc_feature
<222> LOCATION: (8)..(8)
<223> OTHER INFORMATION: Xaa represents a tyrosine sulfonate
<220> FEATURE:
<221> NAME/KEY: misc_feature
<222> LOCATION: (10)..(10)
<223> OTHER INFORMATION: Xaa represents a tyrosine sulfonate
<220> FEATURE:
<221> NAME/KEY: misc_feature
<222> LOCATION: (12)..(12)
<223> OTHER INFORMATION: Xaa represents a tyrosine sulfonate

<400> SEQUENCE: 5

Ser Xaa Asp Xaa Ser Xaa Asp Xaa Ser Xaa Asp Xaa Ser
1               5                   10

<210> SEQ ID NO 6
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (2)..(2)
<223> OTHER INFORMATION: Xaa represents a p-Carboxymethyl Phe
<220> FEATURE:
<221> NAME/KEY: misc_feature
<222> LOCATION: (4)..(4)
<223> OTHER INFORMATION: Xaa represents a p-Carboxymethyl Phe
<220> FEATURE:
<221> NAME/KEY: misc_feature
<222> LOCATION: (6)..(6)
<223> OTHER INFORMATION: Xaa represents a p-Carboxymethyl Phe
<220> FEATURE:
<221> NAME/KEY: misc_feature
<222> LOCATION: (8)..(8)
<223> OTHER INFORMATION: Xaa represents a p-Carboxymethyl Phe
```

```
<220> FEATURE:
<221> NAME/KEY: misc_feature
<222> LOCATION: (10)..(10)
<223> OTHER INFORMATION: Xaa represents a p-Carboxymethyl Phe
<220> FEATURE:
<221> NAME/KEY: misc_feature
<222> LOCATION: (12)..(12)
<223> OTHER INFORMATION: Xaa represents a p-Carboxymethyl Phe

<400> SEQUENCE: 6

Ser Xaa Asp Xaa Ser Xaa Asp Xaa Ser Xaa Asp Xaa Ser
1               5                   10

<210> SEQ ID NO 7
<211> LENGTH: 14
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (2)..(2)
<223> OTHER INFORMATION: Xaa represents a Aminosuberic acid
<220> FEATURE:
<221> NAME/KEY: misc_feature
<222> LOCATION: (4)..(4)
<223> OTHER INFORMATION: Xaa represents a Aminosuberic acid
<220> FEATURE:
<221> NAME/KEY: misc_feature
<222> LOCATION: (6)..(6)
<223> OTHER INFORMATION: Xaa represents a Aminosuberic acid
<220> FEATURE:
<221> NAME/KEY: misc_feature
<222> LOCATION: (8)..(8)
<223> OTHER INFORMATION: Xaa represents a Aminosuberic acid
<220> FEATURE:
<221> NAME/KEY: misc_feature
<222> LOCATION: (10)..(10)
<223> OTHER INFORMATION: Xaa represents a Aminosuberic acid
<220> FEATURE:
<221> NAME/KEY: misc_feature
<222> LOCATION: (13)..(13)
<223> OTHER INFORMATION: Xaa represents a Aminosuberic acid

<400> SEQUENCE: 7

Ser Xaa Asp Xaa Ser Xaa Asp Xaa Phe Xaa Phe Asp Xaa Ser
1               5                   10

<210> SEQ ID NO 8
<211> LENGTH: 13
<212> TYPE: PRT
<213> ORGANISM: artificial
<220> FEATURE:
<223> OTHER INFORMATION: artificial peptide

<400> SEQUENCE: 8

Ser Tyr Asp Tyr Ser Tyr Asp Tyr Ser Tyr Asp Tyr Ser
1               5                   10

<210> SEQ ID NO 9
<211> LENGTH: 13
<212> TYPE: PRT
<213> ORGANISM: artificial
<220> FEATURE:
<223> OTHER INFORMATION: artificial peptide

<400> SEQUENCE: 9

Asp Asp Asp Asp Asp Asp Asp Asp Asp Asp Asp Asp Asp
1               5                   10

<210> SEQ ID NO 10
```

```
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (1)..(13)
<223> OTHER INFORMATION: Xaa represents a sulfo tyrosine

<400> SEQUENCE: 10

Xaa Xaa Xaa Xaa Xaa Xaa Xaa Xaa Xaa Xaa Xaa Xaa Xaa
1               5                   10

<210> SEQ ID NO 11
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (1)..(13)
<223> OTHER INFORMATION: Xaa represents a tyrosine sulfonate

<400> SEQUENCE: 11

Xaa Xaa Xaa Xaa Xaa Xaa Xaa Xaa Xaa Xaa Xaa Xaa Xaa
1               5                   10

<210> SEQ ID NO 12
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (1)..(13)
<223> OTHER INFORMATION: Xaa represents a Aminosuberic acid

<400> SEQUENCE: 12

Xaa Xaa Xaa Xaa Xaa Xaa Xaa Xaa Xaa Xaa Xaa Xaa Xaa
1               5                   10

<210> SEQ ID NO 13
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (1)..(13)
<223> OTHER INFORMATION: Xaa represents a p-Carboxymethyl Phe

<400> SEQUENCE: 13

Xaa Xaa Xaa Xaa Xaa Xaa Xaa Xaa Xaa Xaa Xaa Xaa Xaa
1               5                   10

<210> SEQ ID NO 14
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: NH2-(CH2)3-CO-Ser
<220> FEATURE:
<221> NAME/KEY: misc_feature
```

<222> LOCATION: (2)..(2)
<223> OTHER INFORMATION: Xaa represents a sulfo tyrosine
<220> FEATURE:
<221> NAME/KEY: misc_feature
<222> LOCATION: (4)..(4)
<223> OTHER INFORMATION: Xaa represents a sulfo tyrosine
<220> FEATURE:
<221> NAME/KEY: misc_feature
<222> LOCATION: (6)..(6)
<223> OTHER INFORMATION: Xaa represents a sulfo tyrosine
<220> FEATURE:
<221> NAME/KEY: misc_feature
<222> LOCATION: (8)..(8)
<223> OTHER INFORMATION: Xaa represents a sulfo tyrosine
<220> FEATURE:
<221> NAME/KEY: misc_feature
<222> LOCATION: (10)..(10)
<223> OTHER INFORMATION: Xaa represents a sulfo tyrosine
<220> FEATURE:
<221> NAME/KEY: misc_feature
<222> LOCATION: (12)..(12)
<223> OTHER INFORMATION: Xaa represents a sulfo tyrosine

<400> SEQUENCE: 14

Ser Xaa Asp Xaa Ser Xaa Asp Xaa Ser Xaa Asp Xaa Ser
1               5                   10

<210> SEQ ID NO 15
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: NH2-(CH2)3-CO-Ser

<400> SEQUENCE: 15

Ser Tyr Asp Tyr Ser Tyr Asp Tyr Ser Tyr Asp Tyr Ser
1               5                   10

<210> SEQ ID NO 16
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: NH2-(CH2)3-CO-Ser
<220> FEATURE:
<221> NAME/KEY: misc_feature
<222> LOCATION: (2)..(2)
<223> OTHER INFORMATION: Xaa represents a p-Carboxymethyl Phe
<220> FEATURE:
<221> NAME/KEY: misc_feature
<222> LOCATION: (4)..(4)
<223> OTHER INFORMATION: Xaa represents a p-Carboxymethyl Phe
<220> FEATURE:
<221> NAME/KEY: misc_feature
<222> LOCATION: (6)..(6)
<223> OTHER INFORMATION: Xaa represents a p-Carboxymethyl Phe
<220> FEATURE:
<221> NAME/KEY: misc_feature
<222> LOCATION: (8)..(8)
<223> OTHER INFORMATION: Xaa represents a p-Carboxymethyl Phe
<220> FEATURE:
<221> NAME/KEY: misc_feature
<222> LOCATION: (10)..(10)
<223> OTHER INFORMATION: Xaa represents a p-Carboxymethyl Phe
<220> FEATURE:
<221> NAME/KEY: misc_feature
<222> LOCATION: (12)..(12)

<223> OTHER INFORMATION: Xaa represents a p-Carboxymethyl Phe

<400> SEQUENCE: 16

Ser Xaa Asp Xaa Ser Xaa Asp Xaa Ser Xaa Asp Xaa Ser
1               5                   10

<210> SEQ ID NO 17
<211> LENGTH: 14
<212> TYPE: PRT
<213> ORGANISM: artificial
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: NH2-(CH2)3-CO-Ser
<220> FEATURE:
<221> NAME/KEY: misc_feature
<222> LOCATION: (2)..(2)
<223> OTHER INFORMATION: Xaa represents a Aminosuberic acid
<220> FEATURE:
<221> NAME/KEY: misc_feature
<222> LOCATION: (4)..(4)
<223> OTHER INFORMATION: Xaa represents a Aminosuberic acid
<220> FEATURE:
<221> NAME/KEY: misc_feature
<222> LOCATION: (6)..(6)
<223> OTHER INFORMATION: Xaa represents a Aminosuberic acid
<220> FEATURE:
<221> NAME/KEY: misc_feature
<222> LOCATION: (8)..(8)
<223> OTHER INFORMATION: Xaa represents a Aminosuberic acid
<220> FEATURE:
<221> NAME/KEY: misc_feature
<222> LOCATION: (10)..(10)
<223> OTHER INFORMATION: Xaa represents a Aminosuberic acid
<220> FEATURE:
<221> NAME/KEY: misc_feature
<222> LOCATION: (13)..(13)
<223> OTHER INFORMATION: Xaa represents a Aminosuberic acid

<400> SEQUENCE: 17

Ser Xaa Asp Xaa Ser Xaa Asp Xaa Phe Xaa Phe Asp Xaa Ser
1               5                   10

<210> SEQ ID NO 18
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: NH2-(CH2)3-CO-Glu

<400> SEQUENCE: 18

Glu Glu Glu Glu Glu Glu Glu Glu Glu Glu Glu Glu Glu
1               5                   10

<210> SEQ ID NO 19
<211> LENGTH: 13
<212> TYPE: PRT
<213> ORGANISM: artificial
<220> FEATURE:
<223> OTHER INFORMATION: artificial peptide
<220> FEATURE:
<221> NAME/KEY: misc_feature
<222> LOCATION: (2)..(2)
<223> OTHER INFORMATION: Xaa is selected from the group consisting of:
      tyrosine, sulfotyrosine, tyrosine sulfonate , aminosuberic acid,
      and p-carboxymethyl phenylalanine
<220> FEATURE:

```
<221> NAME/KEY: misc_feature
<222> LOCATION: (4)..(4)
<223> OTHER INFORMATION: Xaa is selected from the group consisting of:
      tyrosine, sulfotyrosine, tyrosine sulfonate , aminosuberic acid,
      and p-carboxymethyl phenylalanine
<220> FEATURE:
<221> NAME/KEY: misc_feature
<222> LOCATION: (6)..(6)
<223> OTHER INFORMATION: Xaa is selected from the group consisting of:
      tyrosine, sulfotyrosine, tyrosine sulfonate , aminosuberic acid,
      and p-carboxymethyl phenylalanine
<220> FEATURE:
<221> NAME/KEY: misc_feature
<222> LOCATION: (8)..(8)
<223> OTHER INFORMATION: Xaa is selected from the group consisting of:
      tyrosine, sulfotyrosine, tyrosine sulfonate , aminosuberic acid,
      and p-carboxymethyl phenylalanine
<220> FEATURE:
<221> NAME/KEY: misc_feature
<222> LOCATION: (10)..(10)
<223> OTHER INFORMATION: Xaa is selected from the group consisting of:
      tyrosine, sulfotyrosine, tyrosine sulfonate , aminosuberic acid,
      and p-carboxymethyl phenylalanine
<220> FEATURE:
<221> NAME/KEY: misc_feature
<222> LOCATION: (12)..(12)
<223> OTHER INFORMATION: Xaa is selected from the group consisting of:
      tyrosine, sulfotyrosine, tyrosine sulfonate , aminosuberic acid,
      and p-carboxymethyl phenylalanine

<400> SEQUENCE: 19

Ser Xaa Asp Xaa Ser Xaa Asp Xaa Ser Xaa Asp Xaa Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Anionic polypeptide
<220> FEATURE:
<221> NAME/KEY: misc_feature
<222> LOCATION: (2)..(2)
<223> OTHER INFORMATION: Xaa represents a sulfo tyrosine
<220> FEATURE:
<221> NAME/KEY: misc_feature
<222> LOCATION: (4)..(4)
<223> OTHER INFORMATION: Xaa represents a sulfo tyrosine
<220> FEATURE:
<221> NAME/KEY: misc_feature
<222> LOCATION: (6)..(6)
<223> OTHER INFORMATION: Xaa represents a sulfo tyrosine

<400> SEQUENCE: 20

Ser Xaa Asp Xaa Ser Xaa Asp Tyr Ser Tyr Asp Tyr Ser
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Anionic polypeptide
<220> FEATURE:
<221> NAME/KEY: misc_feature
<222> LOCATION: (8)..(8)
<223> OTHER INFORMATION: Xaa represents a sulfo tyrosine
<220> FEATURE:
<221> NAME/KEY: misc_feature
<222> LOCATION: (10)..(10)
<223> OTHER INFORMATION: Xaa represents a sulfo tyrosine
<220> FEATURE:
<221> NAME/KEY: misc_feature
<222> LOCATION: (12)..(12)
<223> OTHER INFORMATION: Xaa represents a sulfo tyrosine
```

<400> SEQUENCE: 21

Ser Tyr Asp Tyr Ser Tyr Asp Xaa Ser Xaa Asp Xaa Ser
1               5                   10